United States Patent
Miyazaki et al.

(10) Patent No.: US 7,651,859 B2
(45) Date of Patent: Jan. 26, 2010

(54) METHOD OF ANALYZING C-TERMINAL AMINO ACID SEQUENCE OF PEPTIDE

(75) Inventors: Kenji Miyazaki, Minato-ku (JP); Akira Tsugita, Minato-ku (JP); Kenichi Kamijo, Minato-ku (JP); Takuji Nabetani, Chuo-ku (JP)

(73) Assignee: NEC Corporation, Tokyo (JP)

( * ) Notice: Subject to any disclaimer, the term of this patent is extended or adjusted under 35 U.S.C. 154(b) by 654 days.

(21) Appl. No.: 10/538,305

(22) PCT Filed: Dec. 4, 2003

(86) PCT No.: PCT/JP03/15522

§ 371 (c)(1), (2), (4) Date: Jun. 9, 2005

(87) PCT Pub. No.: WO2004/053498

PCT Pub. Date: Jun. 24, 2004

(65) Prior Publication Data

US 2006/0057731 A1    Mar. 16, 2006

(30) Foreign Application Priority Data

Dec. 10, 2002    (JP) .................. 2002-357972

(51) Int. Cl.
*G01N 33/00* (2006.01)

(52) U.S. Cl. ............... 436/89; 436/86; 436/90; 435/23; 530/345

(58) Field of Classification Search ............ None
See application file for complete search history.

(56) References Cited

U.S. PATENT DOCUMENTS 5,952,653 A * 9/1999 Covey et al. ............ 250/288

(Continued)

FOREIGN PATENT DOCUMENTS

JP    05-133958 A    5/1993

(Continued)

OTHER PUBLICATIONS

Tsugita, Akira, et al., Additional possible tools for identification of proteins on one- or two-dimensional electrohoesis, 1998, Electrohoresis, vol. 19, pp. 928-938.*

(Continued)

*Primary Examiner*—Yelena G Gakh
*Assistant Examiner*—Robert Xu
(74) *Attorney, Agent, or Firm*—Sughrue Mion, PLLC

(57) ABSTRACT

The present invention provides, as for a method for analyzing the C-terminal amino acid sequence of a peptide by using a reaction for successively releasing the C-terminal amino acids of the peptide, which method can suppress, when successively releasing the C-terminal amino acids of a peptide of long amino acid length, such a undesirable side reaction as cleavage of peptide bond in the intermediate position of the peptide and can carry out the chemical treatment thereof under widely applicable conditions, a following method wherein a dry sample of a peptide with long amino acid length is beforehand subjected to an N-acylation treatment; by using a reaction reagent where an alkanoic acid anhydride is combined with a small amount of a perfluoroalkanoic acid, successive release of C-terminal amino acids is conducted under mild conditions; a hydrolysis treatment is applied; then, selective fragmentization at site of arginine residue is performed by digestion by trypsin; thereafter, decreases in molecular weight are measured for the C-terminal side fragments derived from a series of reaction products by analysis in negative mode of a MALDI-TOF-MS apparatus; thereby, the C-terminal amino acid sequence of the peptide sample is identified.

8 Claims, 8 Drawing Sheets

Truncation in Gel

Dehydration Treatment
1mL CH₃CN

Swelling Treatment
In Non-aqueous syatem
1mL 1%HFBA, 10%(CH₃CO)₂O
Solution in Formamide
50ºC, 3 hours

U.S. PATENT DOCUMENTS 6,046,053 A * 4/2000 Tsugita et al. .............. 436/89

FOREIGN PATENT DOCUMENTS

| JP | 06-027113 A | 2/1994 |
| JP | 10-293130 A | 11/1998 |
| JP | 2000-146983 A | 5/2000 |
| JP | 2002-189029 A | 7/2002 |
| JP | 2003-279581 A | 10/2003 |
| WO | 03-081255 A1 | 10/2003 |

OTHER PUBLICATIONS

Tsugita, Akira, et al., Reaction of pentafluoropropionic anhydride vapor on polypeptide as revealed by mass spectrometry. A carboxypeptidase mimetic degradation, 1992, Chemisry Letters, pp. 235-238.*

Vogt, S., et al., Effective esterification of carboxymethyl cellulose in a new non-aqueous swelling system, 1996, Polymer Bulletin, vol. 36, p. 549-555.*

Tsugita, A. et al., C-terminal sequencing of protein, Eur. J. Biochem. 206, 691-696 (1992).

Tsugita, A. et al., Chemistry Letters, The Chemical Society of Japan. 1992, 235-238.

Takamoto, K. et al., Carboxy-terminal degradation of peptides using perfluoroacyl anhydrides, Eur. J. Biochem. 228, 362-372 (1995).

"C-terminal sequencing method for proteins in polyacrylamide gel by the reaction of acetic anhydride", Kenji Miyazaki, et al., Proteomics Research Center, Fundamental and Environmental Research Laboratories, NEC Corp., Tsukuba, Japan, 2006, vol. 6, No. 7, pp. 2026-2033.

Miyazaki K. et al, "Musui sakusan joki ni yoru c mattan hairetsu kaiseki (2P-155)", SEIGAQ (Seikagaku—the Journal of Japanese Biochemistry Society) Nippon Seikagakkai (Japanese Biomedical Society), Tokyo, JP, vol. 74, No. 8, Aug. 25, 2002, p. 739.

* cited by examiner

Fig. 1

| Pre-treatment | Main Reaction | Post-treatment |
|---|---|---|
| Peptide →(Dry up)→ CH3CO-Peptide | →(Dry up)→ (CH3CO)n-Peptide(dehydro) | →(Dry up)→ Truncated CH3CO-Peptide → MALDI-TOF-MS |
| 5% CH3COOH | 1-20% CF3(CF2)nCOOH | 1-20% DMAE aq. |
| 95% CH3CO-O-CH3CO (acetic anhydride) | 80-99% CH3CO-O-CH3CO (acetic anhydride) | 60-100C, 0.5-2h |
| (+ 1% Pyridine) | | or |
| 50C, 1h | 20-60C, 1-16h | 10% Pyridine aq. |
| | n=0, 1, 2 | 100C, 0.5h |

Fig. 7 myoglobin − horse

[1 − 153] mass = 17738.180
Cleavage at R

Small polar :  D(7)   E(13)  N(3)   Q(6)
Large polar :  K(19)  R(2)   H(11)
Small non-polar :  S(5)   T(7)   A(15)  G(15)
Large non-polar :  L(17)  I(9)   V(7)   M(2)   F(7)   Y(2)   W(2)
Special :  C(0)   P(4)

K[16] + 42.04    K[42] + 42.04    K[45] + 42.04    K[47] + 42.04
K[50] + 42.04    K[56] + 42.04    K[62] + 42.04    K[63] + 42.04
K[77] + 42.04    K[78] + 42.04    K[79] + 42.04    K[87] + 42.04
K[96] + 42.04    K[98] + 42.04    K[102] + 42.04   K[118] + 42.04
K[133] + 42.04   K[145] + 42.04   K[147] + 42.04

```
  1 G L S D G E W Q Q V L N V W G K V E A D I A G H G Q E V L I  30
 31 R l f t g h p e t l e K f d K f K h l K t e a e m K a s e d  60
 61 l K K h g t v v l t a l g g i l K K K g h h e a e l K p l a  90
 91 q s h a t K h K i p i K y l e f i s d a i i h v l h s K h p 120
121 g n f g a d a q g a m t K a l e l f r N D I A A K Y K E L G 150
151 F Q G                                                     153
```

(1) [1−31] = 3444.742     (2) [32−139] = 12692.649     (3) [140−153] = 1636.809

METHOD OF ANALYZING C-TERMINAL AMINO ACID SEQUENCE OF PEPTIDE

TECHNICAL FIELD

The present invention relates to a method for analysis of C-terminal amino acid sequence of peptide, more typically to a method comprising steps of releasing the C-terminal amino acids of a peptide successively by chemical technique, determining the molecular weights of the reaction products obtained therefrom by mass spectrometry, and identifying the C-terminal amino acid sequence of the peptide, for example, a peptide having a large number of amino acid residues, such as protein, based on the decreases in molecular weight that are caused by a series of amino acids eliminated successively.

BACKGROUND ART

With respect to peptides and proteins collected from nature, the identification of their amino acid sequences are essential information to make a study of the biological properties and functions of the peptides and proteins in question. Currently, the full-length amino acid sequences for peptides and proteins are determined as deduced amino acid sequences, based on corresponding gene information thereof, for instance, nucleotide sequences of the genomic genes or c-DNAs produced from m-RNAs which encode their peptides. However, in identifying the genomic genes or the c-DNAs produced from m-RNAs which encode these peptides, the knowledge of partial amino acid sequences of the peptides is still required.

It is generally considered that, as the knowledge of the partial amino acid sequences of peptide, the N-terminal amino acid sequence and C-terminal amino acid sequence of peptide are particularly useful. Specifically, for example, in selecting a c-DNA which encodes an aimed peptide from a c-DNA library prepared from a large number of m-RNAs, if the N-terminal amino acid sequence and C-terminal amino acid sequence thereof are known, the aimed c-DNA can be selected by using nucleic acid probes that are produced based on said amino acid sequences of the two termini. Alternatively, the aimed c-DNA can be amplified selectively by applying PCR with use of oligonucleotide primers that are produced based on the amino acid sequences of the two termini.

As the method for analyzing the N-terminal amino acid sequence of a peptide, there has been conventionally used a method of subjecting a pure peptide sample obtained by isolation and purification to Edman degradation to successively degrade the N-terminal amino acids therefrom and identify the resulting amino acid derivatives. Meanwhile, as the method for analyzing the C-terminal amino acid sequence of a peptide, there has been proposed a method comprising steps of releasing the C-terminal amino acids successively from such a pure peptide sample by means of chemical technique and identifying the C-terminal amino acids released thereby, based on the molecular weight differences between the original peptide and truncated peptides that are obtained as reaction products therefrom. As the process for releasing the C-terminal amino acids successively by means of chemical technique, there is proposed, for example, a process comprising steps of allowing a vapor generated from a high concentration aqueous solution of pentafluoropropanoic acid ($CF_3CF_2COOH$) or a high concentration aqueous solution of heptafluorobutanoic acid ($CF_3CF_2CF_2COOH$), to act on a dried pure peptide sample under heating up condition of at 90° C., and thereby carrying out selective hydrolysis of the C-terminal amino acids, which is enhanced by said perfluoroalkanoic acid [Tsugita, A. et al., Eur. J. Biochem. 206, 691-696 (1992)]. In addition, there is also proposed a process using, in place of said high concentration aqueous solution of a perfluoroalkanoic acid, a solution of pentafluoropropanoic acid anhydride [$(CF_3CF_2CO)_2O$] in acetonitrile or a solution of heptafluorobutanoic acid anhydride [$(CF_3CF_2CF_2CO)_2O$] in acetonitrile, which process comprises steps of allowing a vapor generated from the solution, to act on a dried peptide under cooling down condition, for example, at $-18°$ C., and thereby conducting selective release of the C-terminal amino acids, which is forced by said perfluoroalkanoic acid anhydride [Tsugita, A. et al., Chem. Lett. 1992, 235-238; Takamoto, K. et al., Eur. J. Biochem. 228, 362-372 (1995)].

In said method for selectively releasing the C-terminal amino acids by allowing a perfluoroalkanoic acid or a perfluoroalkanoic acid anhydride, which are supplied in vapor phase as a vapor thereof, to act on a dried pure peptide sample, it has been reported that an oxazolone ring structure is once formed from the C-terminal amino acids, as a reaction intermediate, through a dehydration reaction shown by the following reaction scheme (I):

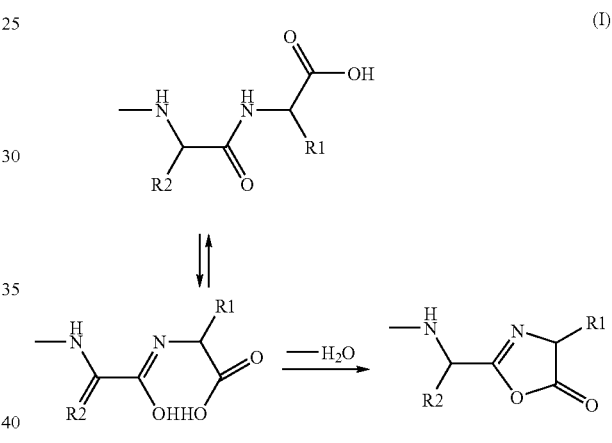

and then, the perfluoroalkanoic acid acts on the oxazolone ring to give rise to a reaction shown by the following reaction scheme (II):

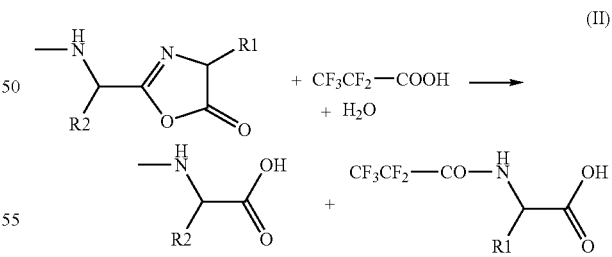

as a result, reaction of selectively releasing the C-terminal amino acids therefrom is achieved.

As the above reaction of selectively releasing the C-terminal amino acid proceeds successively, there is obtained, at a timing when a given treatment time has passed, a mixture comprising a series of reaction products in which one to ten odd amino acid residues have been removed from the C-terminus of the original peptide, respectively. This mixture comprising a series of reaction products is subjected to mass spectrometry to measure the masses of the ion species derived from the reaction products, whereby can be obtained a series of peaks exhibiting the mass differences, which reflect the C-terminal amino acid sequence. Specifically explaining, the individual reaction products are formed in reaction of successively releasing the C-terminal amino acids from the original peptide; hence, for example, a set of reaction products including several members in series, where up to several amino acid residues have been removed from the original peptide, are subjected to mass spectrometry and, thereby, the masses of corresponding ion species thereto can be analyzed collectively, which enables determination of C-terminal amino acid sequence of such several amino acid residues at one time.

Incidentally, for example, the information of C-terminal amino acid sequence used in production of nucleic acid probe or primer may originally be, in terms of the nucleotide sequence which codes such amino acid sequence, about 18 to 24 bases and accordingly about 6 to 8 amino acids. The identification of C-terminal amino acid sequence of up to ten odd amino acid residues is required only in very rare cases. Therefore, the above methods for preparation of treated sample comprising a series of reaction products, in which all the removals extending up to 10 amino acid resides are included, by the reaction of releasing the C-terminal amino acids from the dried peptide, where a vapor of a perfluoroalkanoic acid or a perfluoroalkanoic acid anhydride are supplied in vapor phase and allowed to act thereon, are suitable for the above-mentioned purposes.

DISCLOSURE OF THE INVENTION

Meanwhile, when a peptide to be examined is, for example, a peptide having a large number of amino acid residues such as a protein, the molecular weight of the original peptide per se exceeds an molecular weight range to which mass spectrometry is applicable, or the change in formula weight due to one amino acid residue is relatively small in relation to the large molecular weight of the original peptide per se, which leads to the decreased accuracy of measurement of differences in molecular weight; therefore, in such a case, the following idea has been studied. Specifically explaining, used is the idea in such a form that the mixture containing a series of reaction products obtained by the above-mentioned reaction for successive release of C-terminal amino acids, in which products one to ten odd amino acid residues have been removed respectively from the C-terminus of an original peptide, is subjected to enzymatic digestion of long peptide chain by using a protease having a site selectivity for cleavage, e.g. trypsin, which is applicable for selective cleavage of a peptide chain at the specific amino acid sites thereof; thereafter, the peptide fragments resulting from are subjected to analysis by mass spectrometry. That is, in the mixture of peptide fragments obtained by application of such enzymatic digestion thereto, are included a C-terminal peptide fragments derived from the original peptide, and a group of C-terminal peptide fragments derived the series of said reaction products in which one to ten odd amino acid residues have been removed respectively from the C-terminus thereof; by applying mass spectrometry to the group of the C-terminal peptide fragments derived from the original peptide as well as the series of reaction products, to measure the mass of each of the ion species of the C-terminal peptide fragments derived form the reaction products, there can be measured, at a sufficiently high resolution for molecular weight, a series of peaks exhibiting the differences in mass, which may reflect the C-terminal amino acid sequence in question.

Meanwhile, the above-mentioned methods comprising such steps of supplying a vapor of a perfluoroalkanoic acid or a perfluoroalkanoic acid anhydride in vapor phase and allowing them to act on a dried peptide are useful technique for identifying the C-terminal amino acid sequence thereof; however, when extending application of the methods as a procedure for a wide use, the methods have been found to have various practical problems described below, in the case where a peptide to be examined is a peptide having a large number of amino acid residues, such a protein.

The first problem is described. In the above-mentioned method with use of a high concentration aqueous solution of a perfluoroalkanoic acid, which allows a vapor of the perfluoroalkanoic acid to act on a dried peptide under heating up condition, for example, at 90° C., there may occur a side reaction in which, at the serine residue [—NH—CH(CH$_2$OH)—CO—] in the peptide, an N,O-acyl rearrangement reaction proceeds between the amino group (—NH—) on its α-position and the hydroxyl group (—OH) on its β-position, subsequently, hydrolysis proceeds, which results in cleavage of peptide taking place at the N-terminal of the serine residue. Depending upon the conditions used, there may also occur a side reaction in which, at the threonine residue [—NH—CH(CH(CH$_3$)OH)—CO—] having a hydroxyl group (—OH) on its β-position, hydrolysis proceeds through a similar mechanism, which results in cleavage of peptide taking place at the N-terminal of the threonine residue. There may further occur a side reaction in which, at the aspartic acid residue [—NH—CH(CH$_2$COOH)—CO—] in the peptide, peptide bond rearrangement from C-terminal carboxy group to carboxy group on its β-position and subsequent hydrolysis proceed, which results in cleavage of peptide taking place at the C-terminus of the aspartic acid residue.

When the cleavage of long peptide chain due to such side reactions happens to occur, selective release of C-terminal amino acids progresses simultaneously even as for the resulting N-terminal peptide fragments therefrom. On some occasions, the co-existence of reaction products that are originated from these side reactions may be a factor interfering with the measurement, when conducting analysis of intended reaction products by mass spectrometry.

Further, even when there occurs no cleavage of original peptide chain but when there is formed a branched type peptide wherein the N-terminal portion of peptide is linked to the hydroxyl group (—OH) on the β-position thereof, which leads to loss of amide bond at the site, there is no formation of oxazolone ring structure therefrom, and accordingly selective release of C-terminal amino acid make no further progress thereafter.

On the other hand, in the above-mentioned method with use of an acetonitrile solution of a perfluoroalkanoic acid anhydride, which allows a vapor of the perfluoroalkanoic acid anhydride generated from the solution to act on a dried peptide under cooling down condition, for example, at −18° C., no water molecule being vaporized from the solution is present in said system and, therefore, the method has such an advantage that the occurrence of the above-mentioned side reactions can be avoided effectively. However, since the reactivity of the perfluoroalkanoic acid anhydride used is high, effective suppression of undesired side reactions is more difficult when the treatment temperature rises higher; therefore, the treatment temperature is required to be kept at such a low temperature as, for example, −18° C. In other words, when the control of the treatment temperature is not enough, there is a high possibility that undesired side reactions are advanced thereby; therefore, in this view, it may be considered that the method still has somewhat weakness in the wide applicability and leaves a room to be improved further. In addition, when water condensation takes place in association with cooling, the resulting water gives rise to deterioration of the reagent used, i.e. deactivation of the perfluoroalkanoic acid anhydride used, which may result in a reduced reactivity on occasion, and thus there remains some anxiety that it may happen to become a serious problem in practical application.

The second problem is described. In the case where a peptide to be examined is a peptide having a large number of amino acid residues, such as a protein, it has been studied to employ such a manner in which after the reaction for releasing the C-terminal amino acids of the peptide selectively is finished, the treatment for enzymatic digestion by using a protease having a site selectivity for cleavage is added, and then measurement of the molecular weights of the C-terminal peptide fragments obtained is carried out. In this case, however, a plurality of the peptide fragments from the portion of the N-terminal side, which are inevitably side-produced by the enzymatic cleavage, will be observed coincidentally on the mass spectra measured. Therefore, there is looked forward to the proposal of a method for analysis of the mass spectra measured, which can distinguish, at a high accuracy, spectrum peaks for the C-terminal peptide fragments derived from the original peptide and a series of reaction products thereof, from spectrum peaks for N-terminal peptide fragments and subsequently can determine, at a high precision, the individual molecular weights for the C-terminal peptide fragments derived from the original peptide and the series of reaction products thereof.

The present invention solves the above-mentioned problems and aims at providing a method for reaction to release the C-terminal amino acids successively, with use of which method, when a reaction mechanism via formation of oxazolone ring structure as explained above is used to release the C-terminal amino acids from a long peptide chain, undesired side reactions such as cleavage of peptide bond somewhere along the peptide chain can be suppressed and further said chemical treatment itself can be carried out under widely applicable conditions. The present invention also aims at providing a method for easier analysis of C-terminal amino acid sequence of a long peptide chain, wherein there is combined, with the above-mentioned method for reaction to release the C-terminal amino acids successively, a treatment for enzymatic cleavage using such a protease as, when an original peptide and a series of reaction products obtained therefrom are subjected to an enzymatic cleavage treatment using a protease having a site selectivity for cleavage and the resulting peptide fragments are subjected to mass spectrometry, can distinguish more easily the intended peaks for the C-terminal peptide fragments derived from the original peptide and the series of reaction products thereof, from the peaks for other peptide fragments also obtained by enzymatic digestion.

The present inventors made an intensive study and examination continuously in order to solve the above-mentioned problems. As a result, it was concluded that the undesired reactions seen in the case of the method, where a high concentration aqueous solution of a perfluoroalkanoic acid is used to allow a vapor of the perfluoroalkanoic acid therefrom to act on a dried peptide under heating up conditions, for example, at 90° C., occur because the vapor of a perfluoroalkanoic acid as well as water molecule, both vaporized from the high concentration aqueous solution of the perfluoroalkanoic acid, are present in the reaction system, for example, at the serine residue [NH—CH(CH$_2$OH)—CO—] in the peptide, the N,O-acyl rearrangement reaction between the amino group (—NH—) on its α-position and the hydroxy group (—OH) on its β-position is promoted under said heating conditions and the hydrolysis of the ester formed thereby is also advanced by the help of water molecules co-existing in the reaction system. Meanwhile, in the case of the method, where an acetonitrile solution of a perfluoroalkanoic acid anhydride is used to allow a vapor of the perfluoroalkanoic acid anhydride therefrom to act on a dried peptide under cooling down conditions, for example, at −18° C., it has been confirmed that although there is no water molecule in the reaction system, such a high reactivity of the perfluoroalkanoic acid anhydride per se invites a rapid increase in the frequency of undesired side reactions relative to rising up of the treatment temperature.

Based on the above finding, the present inventors searched such reaction conditions as, without using any water solvent working as source for feeding water molecules to the reaction system and further without using any reagent with such high reactivity as perfluoroalkanoic acid anhydride, an oxazolone ring structure can be formed from the C-terminal amino acids of peptide, as an reaction intermediate and then reaction of selectively releasing the C-terminal amino acid can be completed in association with cleavage of the oxazolone ring. As a result, it was found that with use of a mixture obtained by adding a small amount of a perfluoroalkanoic acid to an alkanoic acid anhydride, when the perfluoroalkanoic acid and alkanoic acid anhydride, both of vapor phase, supplied form the mixture are allowed to act on a dried peptide, even at a treatment temperature such as 60° C. or less, the formation of oxazolone ring structure can be progressed, and subsequently followed by the reaction of selectively releasing the C-terminal amino acid therefrom, which is resulted from the cleavage of this oxazolone ring. It was also found that as the reactivity of alkanoic acid anhydride is significantly mild as compared with a perfluoroalkanoic acid anhydride, even in the presence of the perfluoroalkanoic acid, it is far from giving rise to any cleavage in the middle of peptide. Specifically explaining, the alkanoic acid anhydride acts, in the presence of the perfluoroalkanoic acid, on the hydroxy group present on the serine residue [—NH—CH(CH$_2$OH)—CO—] or threonine residue [—NH—CH(CH(CH$_3$)OH)—CO—] in the peptide to make progress preferentially in an O-acylation reaction, which leads to inhibiting the N,O-acyl rearrangement reaction competitively. It was also found that an N-acylation reaction to the amino group of N-terminus proceeds simultaneously and there also proceed, for example, an N-acylation reaction to the amino group on the ε-position of lysine residue [—NH—CH(CH$_2$CH$_2$CH$_2$CH$_2$NH$_2$)—CO—] and an O-acylation reaction to the phenolic hydroxy group of tyrosine residue [—NH—CH(CH$_2$—C$_6$H$_4$—OH)—CO—]. As a result, it was found that since the reactive functional groups such as hydroxy group or amino group on the side chain, which are involved in the rearrangement reaction such as N,O-acyl rearrangement reaction that initiates the cleavage in the middle of peptide, undergo protection and modification, undesired side reactions are avoided and, at a treatment temperature of, for example, 60° C. or less, there selectively proceed only reactions wherein the oxazolone ring structure is formed as the intended reaction intermediate from the C-terminal amino acid, and subsequently followed by the reaction of releasing the C-terminal amino acid in association with the cleavage of the oxazolone ring.

The present inventors further found that the above-mentioned reaction for selective release of C-terminal amino acids using a perfluoroalkanoic acid and an alkanoic acid anhydride, which comprises formation of an oxazolone ring structure and subsequent cleavage of the oxazolone ring, proceeds even when the perfluoroalkanoic acid and the alkanoic acid anhydride are dissolved in a dipolar aprotic solvent and are allowed to act on a target peptide in a liquid phase with no presence of water molecules in the reaction system, at a temperature of, for example, about 40° C. It was also found that the alkanoic acid anhydride acts on hydroxy group in the presence of the perfluoroalkanoic acid and, as a result, an O-acylation reaction proceeds preferentially, which leads to inhibiting the N,O-acyl rearrangement reaction competitively, and there also proceed an N-acylation reaction to amino group, an O-acylation reaction to phenolic hydroxy group, etc. As a result, it was found that since the reactive functional groups such as hydroxy group or amino group on the side chain, which are involved in the rearrangement reaction such as N,O-acyl rearrangement reaction that initiates the cleavage in the middle of peptide, undergo protection and modification, undesired side reactions are avoided and, at a treatment temperature of, for example, 40° C. or less, there selectively proceed only reactions wherein the oxazolone ring structure is formed as the intended reaction intermediate from the C-terminal amino acid, and subsequently followed by the reaction of releasing the C-terminal amino acid in association with the cleavage of the oxazolone ring. It was found that, for example, a peptide subjected to gel electrophoresis and then bound on the gel carrier used can be subjected to a comparable liquid-phase reaction when the water impregnated into the gel carrier has been removed sufficiently and then there has been infiltrated, into the gel carrier for swelling of the gel, a solution obtained by dissolving a perfluoroalkanoic acid and an alkanoic acid anhydride in a dipolar aprotic solvent.

Further, the present inventors confirmed that, when reactive functional groups of peptide, such as hydroxy group and amino group on the side chain, which are involved in the rearrangement reaction such as N,O-acyl rearrangement reaction that initiates the cleavage in the middle of peptide, undergo protection and modification by O-acylation to hydroxy group and N-acylation to amino group and then there is carried out a reaction of selectively releasing the C-terminal amino acids of peptide with use of said perfluoroalkanoic acid and alkanoic acid anhydride, which occurs in association with the formation of oxazolone ring structure and subsequent cleavage of the oxazolone ring, undesired side reactions can be avoided more effectively. Specifically explaining, it was found that, when an alkanoic acid anhydride and an alkanoic acid both of vapor phase supplied from a mixture of the alkanoic acid anhydride with a small amount of the alkanoic acid is allowed to act on a dried peptide sample in a dried atmosphere at a temperature selected in a range of 10° C. to 60° C., it is possible to beforehand apply N-acylation by the acyl group derived from said alkanoic acid anhydride, to the N-terminal amino group of the peptide as well as to the side chain amino group of the lysine residue which may be present in the peptide, and O-acylation also by the same acyl group to the side chain hydroxy group of the peptide. It was also found that even for a peptide bound on a gel carrier, the N-acylation to said amino groups and the O-acylation to said hydroxy group are possible when the water impregnated into the gel carrier has been removed sufficiently and then a solution of an alkanoic acid anhydride dissolved in a dipolar aprotic solvent has been infiltrated into the gel carrier to give rise to swelling of the gel.

Also, the present inventors confirmed the following. That is, at a timing when the reaction for releasing the C-terminal amino acids of peptide is over, there are also present reaction intermediates generated in association with the formation of oxazolone ring structure and subsequent cleavage of the oxazolone ring; it is necessary for the mass spectrometry to be conducted later that the reaction intermediates are subjected to a hydrolysis treatment and the C-termini of reaction products are returned to a form in which carboxy group is exposed; and the hydrolysis treatment can be easily conducted, for example, by contacting the reaction products with an aqueous solution of a basic, nitrogen-containing, aromatic ring compound or a tertiary amine compound. It was also found that, in the hydrolysis treatment using the catalysis of such an organic base, there proceed, in addition to the hydrolysis reaction for cyclic ester in oxazolone ring structure, a hydrolysis reaction for ester in O-acylation-protected hydroxy group, that is, a deprotection in hydroxy group and, meanwhile, there occurs no deprotection in more stable N-acylation protection. Thus, when such a hydrolysis treatment is applied, there remain, in the original peptide chain, N-acylation protections of the N-terminal amino group and the side chain amino group of the lysine residue which may be present in the peptide chain; also in the peptide chain of each reaction product produced from the reaction for releasing C-terminal amino acids, there remain as well, N-acylation protections of the N-terminal amino group and the side chain amino group of the lysine residue which may be present in the peptide chain.

In addition to the above findings, the present inventors confirmed that, when a cleavage treatment is applied to a long peptide chain in which N-acylation protection has been made to the side chain amino group of the lysine group which may be present in the peptide chain, by using trypsin which has a site selectivity for cleavage of C-terminal side peptide bond of lysine or arginine residue, no cleavage of peptide takes place at the N-acylated lysine residue and there are obtained peptide fragments derived from cleavage at the arginine residue. More specifically explaining, by applying such a cleavage treatment by trypsin, there can be obtained, from a mixture of an original peptide chain and peptide chains of a series of the reaction products produced by a reaction for releasing C-terminal amino acids from the peptide chain, peptide fragments (which are common fragments) each having a partial amino acid sequence containing one arginine residue at the C-terminus and a group of C-terminal side peptide fragments each derived from C-terminal side partial amino acid sequence and containing no arginine residue. In this case, the present inventors concluded that, with respect to the average occurrence of arginine residue in peptide chain, for example, a long peptide chain of about 200 amino acids contain at least only 4 or more arginine residues and at most only about 10 arginine residues and that the common peptide fragments each having one arginine residue at the C-terminus contain about 4 to 10 amino acids and the C-terminal side peptide fragments derived from the original peptide contain at least 15 but 50 or less amino acids, at a high probability.

Moreover, the present inventors proved experimentally that, in the molecular weight measurement for various peptide fragments based on the cationic species and anionic species all generated from ionization treatments to the fragments, by means of MALDI-TOF-MS (Matrix Assisted Laser Desorption Ionization Time-of-Flight Mass Spectrometry), there is apparently a general tendency that, when the peptide fragments have a cationic amino acid residue, particularly an arginine residue at the C-terminus, the peak intensity in the molecular weight measurement based on cationic species is significantly high relative to the corresponding peak intensity in the molecular weight measurement based on anionic species and, when the peptide fragments have no cationic amino acid residue at the C-terminus, the peak intensity in the molecular weight measurement based on anionic species is significantly high relative to the corresponding peak intensity in the molecular weight measurement based on cationic species. Further, the present inventors confirmed that, by utilizing the above general tendency proven experimentally, it is possible in the molecular weight measurement based on the cationic species and anionic species all generated from the ionization treatment, according to the MALDI-TOF-MS, to distinguish, with rationality, said common peptide fragments each having one arginine residue at the C-terminus, from said group of C-terminal side peptide fragments derived from C-terminal side partial amino acid sequence and containing no arginine residue, produced from the original peptide and a series of reaction products thereof. That is, the common peptide fragments each obtained by trypsin-induced cleavage and having one arginine residue at the C-terminus are observed as a single peak at a relatively high intensity in the molecular weight measurement based on cationic species and, in the molecular weight measurement based on anionic species, the intensity of the peak corresponding to the common peptide fragments is relatively low; however, by comparing the results of the two measurements, the common peptide fragments can be identified easily. Meanwhile, in the molecular weight measurement based on anionic species, said group of C-terminal side peptide fragments derived from C-terminal side partial amino acid sequence and containing no arginine residue, produced from the original peptide chain and a series of reaction products thereof are observed as a series of peaks at a relatively high intensity and can be identified easily.

Based on a series of the above findings, the present inventors found the following matter; that is, even for a long peptide chain constituting, for example, a variety of proteins, analysis of its C-terminal amino acid sequence can be made more easily by employing a series of steps which comprise:

(1) applying N-acylation protection and O-acylation protection to a target peptide chain, (2) conducting a reaction for selectively releasing the C-terminal amino acids of the acylated peptide chain under the mild reaction conditions selected appropriately depending upon the state in which the acylated peptide chain is present, (3) then, conducting a hydrolysis reaction to the cyclic ester in oxazolone ring structure and a deprotection reaction to the O-acylation protection under mild conditions, (4) applying a trypsin-induced cleavage treatment to a mixture containing the original peptide chain and the peptide chains of a series of reaction products obtained by selective cleavage of C-terminal amino acids of the peptide chain (in all of these peptide chains, N-acylation protection remains), to prepare peptide fragments (common peptide fragments) each having one arginine residue at the C-terminus and a series of C-terminal side peptide fragments derived from the C-terminal side partial amino acid sequence and containing no arginine residue, produced from the original peptide chain and the peptide chains of a series of reaction produces thereof, (5) subjecting a mixture of these peptide fragments to MALDI-TOF-MS to conduct molecular weight measurements for the cationic species and anionic species all generated by an ionization treatment, and comparing the results of the two measurements to distinguish the common peptide fragments each having one arginine residue at the terminus, from said group of C-terminal side peptide fragments containing no arginine residue, produced from the original peptide chain and the peptide chains of a series of reaction produces thereof, and (6) based on the differences in molecular weight between said group of the C-terminal side peptide fragments produced from the original peptide and the peptide chains of a series of reaction products thereof, identifying the C-terminal amino acid sequence of the long peptide chain. Further, the present inventors examined the usefulness of the above finding. As a result, the present invention has been completed.

The present invention has a plurality of different aspects depending upon the state in which a target peptide chain is present, although these aspects are based on a common technical concept. The present invention has a first aspect which is employed, for example, when the target peptide is an isolated dried sample, and a second aspect which is employed when the target peptide is a sample separated by gel electrophoresis and bound on the gel carrier used.

The method for analysis of C-terminal amino acid sequence of peptide according to the first aspect of the present invention is a method for analyzing the C-terminal amino acid sequence of a peptide to be examined, which method comprises the following steps:

a step of preparing a mixture containing a series of reaction products that are obtained from the peptide to be examined by releasing the C-terminal amino acids successively by chemical, a step of analyzing the differences in molecular weight between said series of reaction products and the original peptide by means of mass spectrometry to measure the decreases in molecular weight associated with the successive release of the C-terminal amino acids, and a step of identifying a series of the amino acids removed successively, based on a series of the measured decreases in molecular weight and arranging them from the C-terminus to obtain the information of the C-terminal amino acid sequence of the peptide, wherein said process for releasing the C-terminal amino acids successively comprises at least the following steps:

a pretreatment step, for providing the protection by means of N-acylation, of allowing an alkanoic acid anhydride and an alkanoic acid both of vapor phase, which are supplied from a mixture of the alkanoic acid anhydride with a small amount of the alkanoic acid added thereto, to act on a dry sample of said peptide to be examined in a dry atmosphere at a temperature selected in a range of 10° C. to 60° C. and, thereby, applying, to the N-terminal amino group of the peptide as well as to the amino group on the side chain of the lysine residue which may be included in the peptide, N-acylation by the acyl group derived from the alkanoic acid anhydride, a step of allowing an alkanoic acid anhydride and a perfluoroalkanoic acid both of vapor phase, which are supplied from a mixture of an alkanoic acid anhydride with a small amount of a perfluoroalkanoic acid added thereto, to act on the dry peptide sample after N-acylation protection in a dry atmosphere at a temperature selected in a range of 15° C. to 60° C. and, thereby, releasing the C-terminal amino acids successively in association with a process that at the C-terminus of the peptide, the formation of a 5-oxazolone structure represented by the following general formula (III):

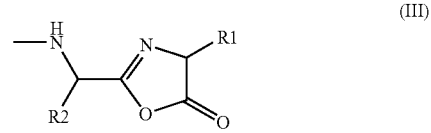

wherein R1 is a side chain of the C-terminal amino acid of the peptide and R2 is a side chain of the amino acid residue positioned just before the C-terminal amino acid, is followed by the cleavage of the 5-oxazolone ring, and a hydrolysis treatment step which comprises applying, to a mixture containing a series of reaction products obtained in said step of releasing the C-terminal amino acids successively, a post-treatment of removing the remaining alkanoic acid anhydride and perfluoroalkanoic acid in a dry state, and then supplying with a basic nitrogen-containing aromatic compound or a tertiary amine compound and water molecules, all of vapor phase, with use of an aqueous solution dissolving the basic nitrogen-containing, aromatic compound or the tertiary amine compound therein, to allow the water molecules to act on the peptides of the reaction products in the presence of the basic nitrogen-containing organic compound to give rise to a hydrolysis treatment, and after that conducting the re-dried up treatment by removing, from the mixture containing a series of reaction products, the remaining basic nitrogen-containing organic compound and water molecules to dry up the mixture, wherein said step of measuring the decreases in molecular weight associated with the successive release of the C-terminal amino acids employs a technique which comprises:

allowing trypsin to act on said mixture, after the re-dried up treatment, containing a series of the reaction products finished by hydrolysis treatment, in a buffer solution, to carry out the treatment for the enzymatic digestion specific to trypsin of said peptide chain which holds N-acylation protection as for the N-terminal amino group of the peptide chain as well as to the amino group on the side chain of the lysine residue that may be contained in the peptide chain, and thereby, conducting selective cleavage of the C-terminal side peptide bond of each arginine residue that present in the peptide chain to complete peptide fragmentization, applying a desalting treatment to remove the buffer solution component, followed by recovering and drying the peptide fragments after the digestion treatment by trypsin, followed by drying, next to that, conducting, as for the dried mixture containing said peptide fragments recovered after the digestion treatment by trypsin, molecular weight measurement for the cationic species as well as molecular weight measurement for anionic species, both of which are generated from the ionization treatment, by means of MALDI-TOF-MS, with respect to the corresponding ion species, which are measured in said molecular weight measurement for the cationic species as well as molecular weight measurement for anionic species, judging that the peaks of the peptide fragments each having an arginine residue at the C-terminus, which fragments are produced by said digestion treatment by trypsin, are peaks that give such intensities that the intensity in the molecular weight measurement for cationic species is relatively larger in comparison with the intensity in the molecular weight measurement for anionic species, and judging that the peaks of the C-terminal peptide fragment derived from the original peptide and the C-terminal peptide fragments derived from a series of the reaction products that are obtained by successive release of the C-terminal amino acids, which fragments are produced by said digestion treatment by trypsin, are peaks that give such intensities that the intensity in the molecular weight measurement for anionic species is relatively larger in comparison with the intensity in the molecular weight measurement for cationic species, and based on a series of the peaks that gives a relatively larger intensity in the molecular weight measurement for anionic species, measuring the decreases in molecular weight associated with the successive release of the C-terminal amino acids.

In the method for analysis according to the first aspect of the present invention, as the alkanoic acid anhydride contained in the mixture of an alkanoic acid anhydride with a small amount of a perfluoroalkanoic acid added thereto, there is preferably used a symmetric anhydride of an alkanoic acid having 2 to 4 carbon atoms. As said symmetric anhydride of an alkanoic acid having 2 to 4 carbon atoms, there is more preferably used a symmetric anhydride of a linear-chain alkanoic acid having 2 to 4 carbon atoms. As the alkanoic acid anhydride contained in said mixture of an alkanoic acid anhydride with a small amount of a perfluoroalkanoic acid added thereto, there is more preferably used, for example, acetic anhydride.

Meanwhile, as the perfluoroalkanoic acid contained in said mixture of an alkanoic acid anhydride with a small amount of a perfluoroalkanoic acid added thereto, there is preferably used a perfluoroalkanoic acid of which pKa is in a range of 0.3 to 2.5. As the perfluoroalkanoic acid contained in said mixture of an alkanoic acid anhydride with a small amount of a perfluoroalkanoic acid added thereto, there can be more preferably used a perfluoroalkanoic acid having 2 to 4 carbon atoms. As the perfluoroalkanoic acid having 2 to 4 carbon atoms, there is more preferably employed, for example, a linear-chain perfluoroalkanoic acid having 2 to 4 carbon atoms.

Further, in said mixture of an alkanoic acid anhydride with a small amount of a perfluoroalkanoic acid added thereto, the content of the perfluoroalkanoic acid is desirably selected in a range of 1 to 20% by volume relative to the total volume of the alkanoic acid anhydride and the perfluoroalkanoic acid. In the treatment using said mixture of an alkanoic acid anhydride with a small amount of a perfluoroalkanoic acid added thereto, said dry atmosphere is much more preferably in a state in which oxygen as well as water have been removed. The dry atmosphere is preferably achieved, for example, by, in an airtight vessel, vacuuming up the atmosphere contained therein. Additionally, in the treatment using said mixture of an alkanoic acid anhydride with a small amount of a perfluoroalkanoic acid added thereto, the temperature is set more desirably at a temperature selected in a range of 15° C. to 50° C.

Meanwhile, the method for analysis of C-terminal amino acid sequence of peptide according to the second aspect of the present invention is a method for analyzing the C-terminal amino acid sequence of a peptide to be examined, which method comprises the following steps:

a step of preparing a mixture containing a series of reaction products that are obtained from the peptide to be examined by releasing the C-terminal amino acids successively by chemical, a step of analyzing the differences in molecular weight between said series of reaction products and the original peptide by means of mass spectrometry to measure the decreases in molecular weight associated with the successive release of the C-terminal amino acids, and a step of identifying a series of the amino acids removed successively, based on a series of the measured decreases in molecular weight and arranging them from the C-terminus to obtain the information of the C-terminal amino acid sequence of the peptide, wherein said process for releasing the C-terminal amino acids successively, as for the sample of the target peptide that has been subjected to separation by gel electrophoresis and is maintained in a state that it is bound on a gel carrier, comprises the following steps:

a step of removing the water solvent impregnated into the gel carrier by dilution with use of a polar aprotic solvent having no solvency for the gel substance and having affinity for water, to conduct a dehydration treatment for the gel carrier, a pretreatment step for the target peptide sample that is still bound on the gel carrier after carrying out said step for dehydration treatment, in which pretreatment step applying N-acylation protection by the acyl group derived from the alkanoic acid constituting said alkanoic acid anhydride, to the N-terminal amino group of the target peptide with use of a solution of an alkanoic acid anhydride dissolved in a dipolar aprotic solvent that is capable of infiltrating into the gel substance and keeping it in a swollen state is conducted by immersing, at a temperature selected in a range of 30° C. to 80° C., the gel carrier in the solution of the alkanoic acid anhydride to allow the alkanoic acid anhydride to act on the target peptide sample that is kept in the bound state; and then removal of said solution is carried out by dilution with use of a polar aprotic solvent having no solvency for the gel substance and having affinity for the alkanoic acid anhydride as well as the dipolar aprotic solvent, to conduct termination of the N-acylation reaction and removal of the reaction reagent therefor;

a step of treatment as for the target peptide sample bound on the gel carrier, after the pretreatment step of N-acylation protection, comprising steps of:

immersing, at a temperature selected in a range of 30° C. to 80° C., the gel carrier in a mixed solution of an alkanoic acid anhydride added with a small amount of a perfluoroalkanoic acid in relative ratio thereto dissolved in a dipolar aprotic solvent that is capable of infiltrating into the gel substance and keeping it in a swollen state, to allow the alkanoic acid anhydride and the perfluoroalkanoic acid to act on the target peptide sample being kept in the bound state; thereby, successive release of the C-terminal amino acids results from the reaction process with use of the mixed solution in which formed is a 5-oxazolone-ring structure represented by the following general formula (III):

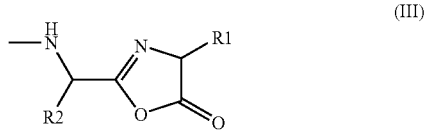

(III)

wherein R1 is a side chain of the C-terminal amino acid of the peptide and R2 is a side chain of the amino acid residue positioned just before the C-terminal amino acid, followed by the cleavage of the 5-oxazolone-ring, and removing the mixed solution used in the reaction for successive release of C-terminal amino acids, by dilution with use of a polar aprotic solvent having no solvency for the gel substance and having affinity for the perfluoroalkanoic acid and the alkanoic acid anhydride as well as the dipolar aprotic solvent, to conduct termination of the releasing reaction and removal of the reaction reagents therefore; and an additional step for hydrolysis treatment and then redehydration treatment, in which step the hydrolysis treatment for said mixture comprising a series of reaction products obtained by the reaction for successive release of C-terminal amino acids is conducted by immersing the gel carrier in an aqueous solution dissolving a basic nitrogen-containing aromatic compound or a tertiary amine compound therein to allow a water molecule to act, in the presence of said basic nitrogen-containing organic compound, on said peptides of the reaction products being still bound on the gel carrier, and then, the redehydration treatment for the gel carrier is performed by removing said aqueous solution infiltrated into the gel carrier by dilution with use of a polar aprotic solvent having no solvency for the gel substance and having affinity for water; and wherein said step of measuring the decreases in molecular weight associated with the successive release of the C-terminal amino acids employs a technique which comprises:

allowing trypsin being soluble in a buffer solution to act on said mixture, after the re-dried up treatment, containing a series of the reaction products finished by hydrolysis treatment to carry out the treatment for the enzymatic digestion specific to trypsin of said peptide chain which holds N-acylation protection as for the N-terminal amino group of the peptide chain as well as to the amino group on the side chain of the lysine residue that may be contained in the peptide chain, and thereby, conducting selective cleavage of the C-terminal side peptide bond of each arginine residue that present in the peptide chain to complete peptide fragmentization, applying a desalting treatment to remove the buffer solution component, followed by recovering and drying the peptide fragments after the digestion treatment by trypsin, next to that, conducting, as for the dried mixture containing said peptide fragments recovered after the digestion treatment by trypsin, molecular weight measurement for the cationic species as well as molecular weight measurement for anionic species, both of which are generated from the ionization treatment, by means of MALDI-TOF-MS, with respect to the corresponding ion species, which are measured in said molecular weight measurement for the cationic species as well as molecular weight measurement for anionic species, judging that the peaks of the peptide fragments each having an arginine residue at the C-terminus, which fragments are produced by said digestion treatment by trypsin, are peaks that give such intensities that the intensity in the molecular weight measurement for cationic species is relatively larger in comparison with the intensity in the molecular weight measurement for anionic species, and judging that the peaks of the C-terminal peptide fragment derived from the original peptide and the C-terminal peptide fragments derived from a series of the reaction products that are obtained by successive release of the C-terminal amino acids, which fragments are produced by said digestion treatment by trypsin, are peaks that give such intensities that the intensity in the molecular weight measurement for anionic species is relatively larger in comparison with the intensity in the molecular weight measurement for cationic species, and based on a series of the peaks that gives a relatively larger intensity in the molecular weight measurement for anionic species, measuring the decreases in molecular weight associated with the successive release of the C-terminal amino acids.

In the method for analysis according to the second aspect of the present invention, as the alkanoic acid anhydride contained in said mixed solution where a small amount of the perfluoroalkanoic acid in relative ratio to the alkanoic acid anhydride is dissolved, there is preferably used a symmetric anhydride of an alkanoic acid having 2 to 4 carbon atoms. As said symmetric anhydride of an alkanoic acid having 2 to 4 carbon atoms, there is more preferably used a symmetric anhydride of a linear-chain alkanoic acid having 2 to 4 carbon atoms. As the alkanoic acid anhydride contained in the mixed solution where a small amount of the perfluoroalkanoic acid in relative ratio to the alkanoic acid anhydride is dissolved, there is more preferably used, for example, acetic anhydride.

Meanwhile, as the perfluoroalkanoic acid contained in the mixed solution where a small amount of the perfluoroalkanoic acid in relative ratio to the alkanoic acid anhydride is dissolved, there is preferably used a perfluoroalkanoic acid of which pKa is in a range of 0.3 to 2.5. As the perfluoroalkanoic acid having 2 to 4 carbon atoms in the mixed solution where a small amount of the perfluoroalkanoic acid in relative ratio to the alkanoic acid anhydride is dissolved, there is preferably used a perfluoroalkanoic acid having 2 to 4 carbon atoms. As the perfluoroalkanoic acid having 2 to 4 carbon atoms, there is more preferably employed a linear-chain perfluoroalkanoic acid having 2 to 4 carbon atoms.

Further, in the mixed solution where a small amount of the perfluoroalkanoic acid in relative ratio to the alkanoic acid anhydride is dissolved, the content ratio of the alkanoic acid anhydride and the perfluoroalkanoic acid is selected more preferably in the range of 1 to 20 volumes of the perfluoroalkanoic acid per 100 volumes of the alkanoic acid anhydride.

BRIEF DESCRIPTION OF THE DRAWINGS

FIG. 1 is a drawing showing a process flow illustrating an example of the detailed operational procedures used when a dry peptide sample is subjected to a treatment for successive release of C-terminal amino acids according to the first aspect of the present invention.

FIG. 7 shows the cleavage sites at the C-terminal side peptide bond of each arginine residue due to the digestion by trypsin, and the lysine residues in which the cleavage at the C-terminal side peptide bond is prevented by the protection with use of N-acetylation, which are included in the amino acid sequences of a peptide chain that is a component of horse myoglobin.

BEST MODE FOR CARRYING OUT THE INVENTION

Figure 2:
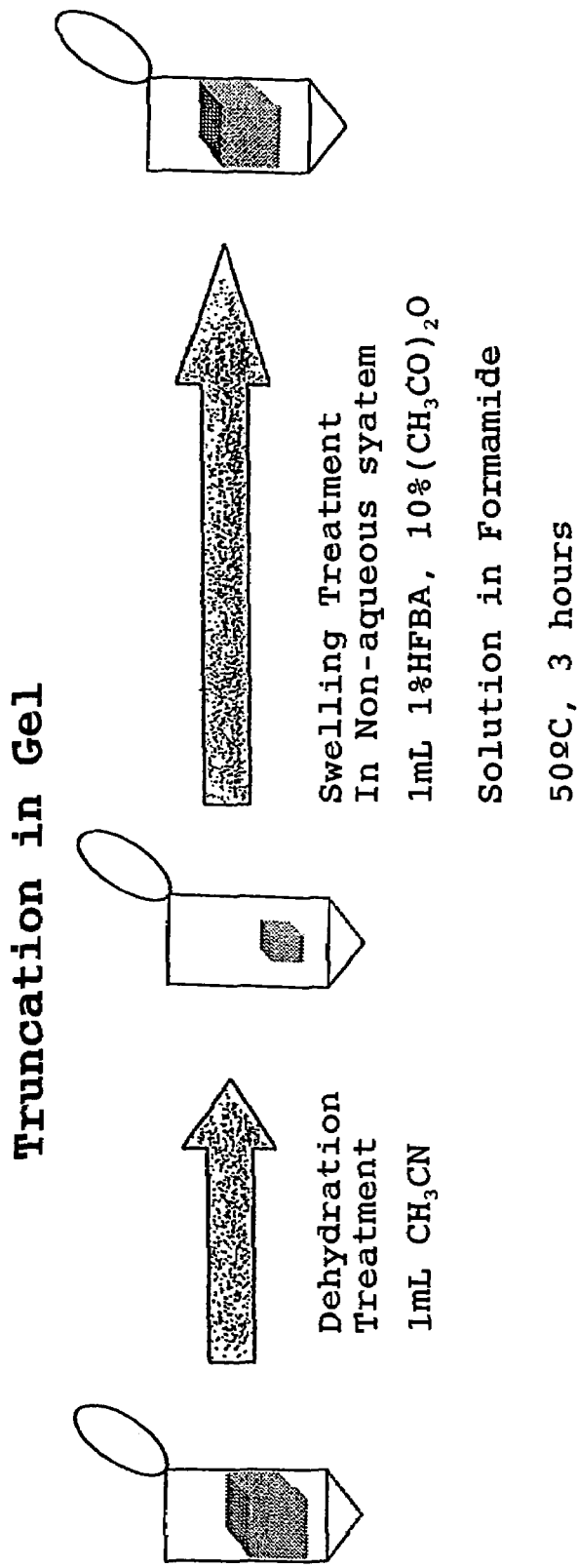
FIG. 2 is a drawing showing a process flow illustrating an example of the detailed operational procedures used when a peptide sample bound on the gel is subjected to a treatment for successive release of C-terminal amino acids according to the second aspect of the present invention.

The present invention is explained in more detail below.

The method for analysis of C-terminal amino acid sequence of peptide according to the present invention basically utilizes a technique which comprises steps of releasing, from a peptide to be examined, its C-terminal amino acids successively to prepare a series of reaction products each having a sequential truncation in peptide chain, and identifying the released amino acids based on the differences between the molecular weights of the C-terminal side peptide fragments derived from the series of reaction products and the molecular weight of the C-terminal side peptide fragment derived form the original peptide peptide, which are discriminated from the fragments obtained by digestion of the series of reaction products and the original peptide by trypsin. More specifically explaining, these C-terminal side peptide fragments that are obtained by digestion by trypsin are terminated at the site specific to trypsin; MALDI-TOF-MS apparatus is employed as means for measuring the molecular weights of the C-terminal side peptide fragments derived from the series of reaction products and the molecular weight of the C-terminal side peptide fragment derived from the original peptide; its mechanism for ionization enables respective measurements for cationic species formed by addition of proton ($H^+$) to peptide fragment and for anionic species formed by detachment of proton ($H^+$) from peptide fragment. Since neither arginine residue nor lysine residue are included in the amino acid residues composing the C-terminal side peptide fragments, in which no mechanism for stabilizing the cationic species that is caused by arginine residue or lysine residue functions; when compared the results of measurement for cationic species with the results of measurement for anionic species, the relative intensities thereof show quite different behavior from that for other peptide fragments in whose amino acid residues an arginine residue or lysine residue is contained; such specific feature thereof is utilized for discrimination and identification of peaks that are attributed to a series of the C-terminal side peptide fragments, from the peaks of a plurality of species measured with use of a MALDI-TOF-MS apparatus.

Therefore, the greatest feature of the method for analysis according to the present invention lies in that, in the step of successively releasing the C-terminal amino acids of an original peptide, the side reaction of peptide bond degradation in the middle of the peptide chain is effectively suppressed and, thereby, there is prevented, into the mixture of all peptide fragments obtained by said treatment for digestion by trypsin, incorporation of peptide fragments resulting from said secondary reaction of peptide bond degradation, other than the common N-terminal side peptide fragments and the intended C-terminal side peptide fragments derived from the series of reaction products, which are all produced by digesting the original peptide with trypsin. It is also a major feature of the method for analysis according to the present invention that, in order to suppress said side reaction of peptide bond degradation in the middle of peptide chain, protection with N-acylation or O-acylation are beforehand applied to the target peptide chain and further, prior to the final digestion by trypsin, the protection with O-acylation is deprotected, while the N-acylation protection on lysine residue is left; thereby, fragmentization by digestion by trypsin is allowed to occur only at the C-terminal side peptide bond of arginine residue, formation of peptide fragments that are unnecessarily divided into small sizes is suppressed, and desired C-terminal side peptide fragments derived from a series of reaction products can have a molecular weight range suitable for measurement by means of MALDI-TOF-MS.

In the reaction for successively releasing C-terminal amino acids from a target peptide used in the present invention, employed is such a process in which, there is used, as a reaction agent, a combination of an alkanoic acid anhydride and a small amount of a perfluoroalkanoic acid, and the alkanoic acid anhydride is allowed to act as a reagent for activation of the C-terminal carboxy group of a target peptide, by means of catalytic function of the perfluoroalkanoic acid exhibiting a high proton donability, in a water-free environment under heated-up condition at a relatively low temperature; at the C-terminus of the peptide, there is once formed a 5-oxazolone structure represented by the following general formula (III):

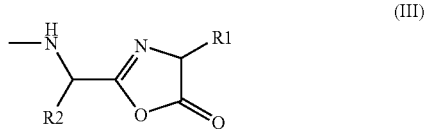

wherein R1 is a side chain of the C-terminal amino acid of the peptide; and R2 is a side chain of the amino acid residue positioned just before the C-terminal amino acid, and then the C-terminal amino acid is released in association with the cleavage of 5-oxazolone ring.

The reaction of the formation of said 5-oxazolone ring is expressed as a whole by the following reaction scheme (I):

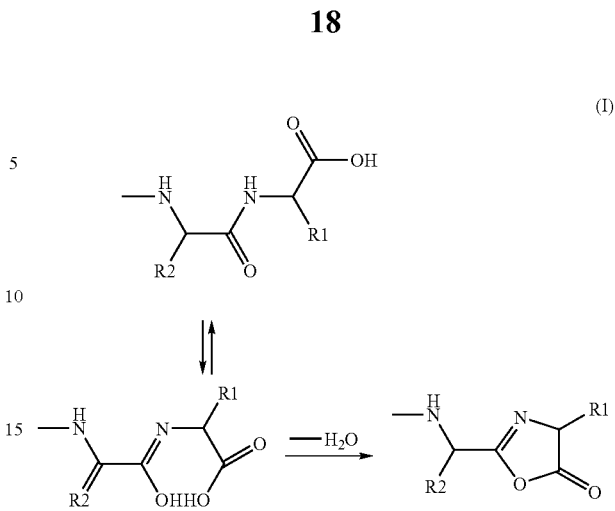

However, in the process for selectively releasing C-terminal amino acids according to the present invention, first, the perfluoroalkanoic acid present in a small amount is allowed to act as a proton donor on the dried peptide at the stage of keto-enol tautomerism represented by the following reaction scheme (Ia):

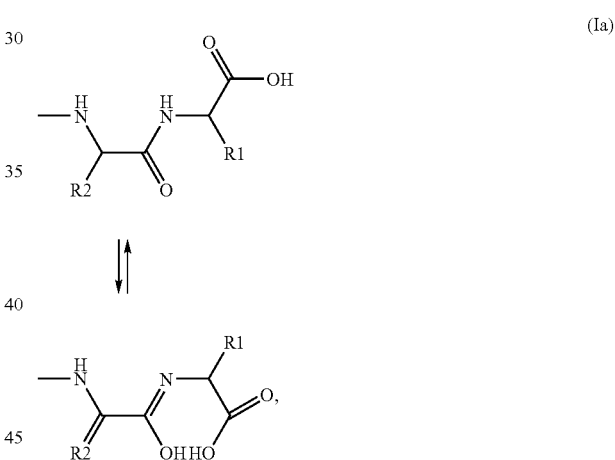

and thereby the ratio of enol form is heightened.

Then, an intramolecular ester bond is formed between the hydroxy group exposed in the enol type and the C-terminal carboxy group to complete the 5-oxazolone ring-formation. In this case, in the process for successive release of C-terminal amino acids according to the present invention, there is used an alkanoic acid anhydride as a reagent for activation of C-terminal carboxy group, and the enol form is converted into, for example, an asymmetric acid anhydride such as shown in the following reaction scheme (Ib):

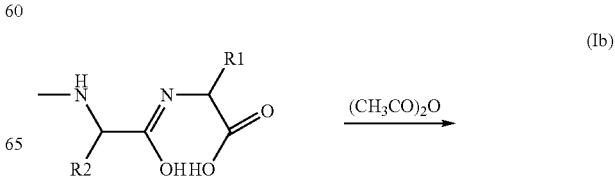

-continued

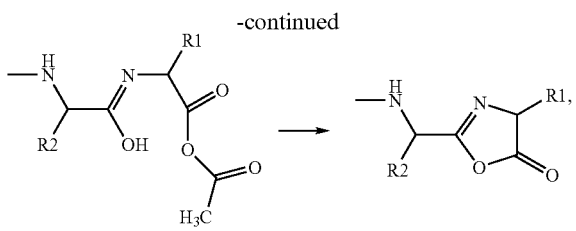

and thus the activated C-terminal carboxy group is involved in the reaction. As a result, such a reaction can proceed even under a mild temperature condition. Meanwhile, since the reaction system is maintained in a water-free state and the alkanoic acid anhydride of relatively low reactivity is used, initiation for the degradation of the peptide bond present in the middle of peptide chain is suppressed under such a mild temperature condition. In the process for selectively releasing C-terminal amino acids according to the present invention, it is understood that, from the once-formed 5-oxazolone ring, the separation of the C-terminal amino acid and the formation of the reaction intermediate for the next stage proceed, for instance, via such a reaction as shown by the following reaction scheme (II'):

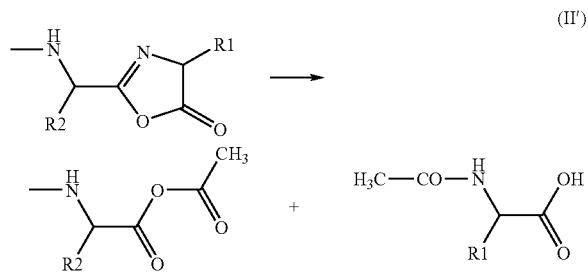

as a result, selective release of C-terminal amino acids is successively advanced in such a way.

Incidentally, there is a certain possibility that the serine residue [—NH—CH(CH$_2$OH)—CO—] and threonine residue [—NH—CH(CH(CH$_3$)OH)—CO—] in peptide chain may give rise to the following side reactions owing to the hydroxy group (—OH) on the side chain: for instance, a N,O-acyl rearrangement reaction between the α-position amino group (—NH—) and the β-position hydroxy group (—OH) is progressed; successively, hydrolysis of the ester bond formed thereby progresses, and thereby peptide cleavage takes place at the N-terminal side of serine residue; further, depending upon the condition, as for the threonine residue [—NH—CH(CH(CH$_3$)OH)—CO—] having a hydroxy group (—OH) at the β-position, hydrolysis is advanced through the similar reaction mechanism that is caused by the N,O-acyl rearrangement reaction, and thereby peptide cleavage takes place at the N-terminal side of threonine residue. In addition, as for peptide having short amino acid sequence, there is also anxiety that the lysine residue [—NH—CH ((CH$_2$)$_4$—NH$_2$)—CO—] in peptide chain may give rise to the following side reaction owing to the amino group (—NH$_2$) on the side chain: when the exchange of amide bond takes place between the α-position amino group (—NH—) and the ε-position amino group (—NH$_2$) both of the lysine residue [—NH—CH(CH$_2$CH$_2$CH$_2$CH$_2$NH$_2$)—CO—] under a heated-up condition, and successively, hydrolysis of the ε-position amide bond formed thereby is advanced, and thereby cleavage of peptide may occur at the N-terminal side of the lysine residue.

In the present invention, the reaction for successively releasing C-terminal amino acids is conducted in a dry state under a mild temperature condition; however, in order to more reliably avoid the above-mentioned side reactions in which the serine residue [—NH—CH(CH$_2$OH)—CO—], threonine residue [—NH—CH(CH(CH$_3$)OH)—CO—] and lysine residue [—NH—CH(CH$_2$CH$_2$CH$_2$CH$_2$NH$_2$)—CO—] is involved, there is conducted, prior to said reaction for successively releasing C-terminal amino acids, a pretreatment step of applying protection with N-acylation and O-acylation.

In the first aspect of the present invention, in this pretreatment step of applying protection with N-acylation and O-acylation, there is allowed to act, on a dry sample of a target peptide, an alkanoic acid anhydride and an alkanoic acid both of vapor phase and supplied from a mixture of an alkanoic acid anhydride and a small amount of an alkanoic acid, in a dry atmosphere at a temperature selected in a range of 10° C. to 60° C.; thereby, the reaction between the amino group (—NH$_2$) or hydroxy group (—OH) and the alkanoic acid anhydride is promoted by utilizing the proton donatability of the alkanoic acid, and N-acylation and O-acylation are achieved. In this case, since the proton donatability that the alkanoic acid has is inferior to the proton donatability that perfluoroalkanoic acid exhibits, it falls quite short of activity required for making progress of the reaction for formation of 5-oxazolone ring at the C-terminus of peptide chain.

In the second aspect of the present invention, a peptide sample bound on a gel carrier is beforehand subjected to a dehydration treatment; then, in the above-mentioned pretreatment step, the gel carrier is immersed, at a temperature selected in a range of 30° C. to 80° C., in a solution of alkanoic acid anhydride dissolved in a dipolar aprotic solvent that is infiltratable into the gel substance and capable of keeping it in swelling state; thereby, the alkanoic acid anhydride is allowed to act on the target peptide sample in a bound state to achieve N-acylation and O-acylation. This liquid-phase reaction in the dipolar aprotic solvent proceeds sufficiently even without utilizing the catalysis of an alkanoic acid having proton donability. In addition, an alkanoic acid is produced in the reaction system in association with the liquid-phase reaction, and the catalytic effect thereof is added, whereby the reaction is gradually promoted. However, since the proton donatability of the alkanoic acid derived in the system is inferior to the proton donatability that perfluoroalkanoic acid shows, it falls quite short of activity required for making progress of the reaction for formation of 5-oxazolone ring at the C-terminus of peptide chain.

In addition, in the present invention, by selecting, in the pretreatment step, such a condition that N-acylation is attained not only to the ε-position amino group (—NH$_2$) of the lysine residue [—NH—CH(CH$_2$CH$_2$CH$_2$CH$_2$NH$_2$)—CO—] but also to the N-terminal amino group of peptide chain, it is possible to provide beforehand, for example, a guard against a case that, when, in the reaction for successive release of C-terminal amino acids, the C-terminal carboxy group has been activated, a reaction with the N-terminal amino group of adjacent peptide chain may happen to take place accidentally. Further, since, when the treatment for hydrolysis is conducted in the post-treatment step, there is selected such a hydrolysis condition that none of the protections with N-acylation to the ε-position amino group (—NH$_2$) of the lysine residue [—NH—CH((CH$_2$)$_3$—NH$_2$)—CO—] and to the N-terminal amino group of peptide chain is deprotected, no enzymatic digestion reaction by trypsin takes place, in the final treatment for digestion by trypsin, at the C-terminus of the lysine residue whose amino group on side chain is protected with N-acylation; and thus the peptide fragments obtained by digestion by trypsin are limited to those fragments obtained by digestion at the C-terminus of arginine residue.

In the present invention, made is good use of such merit that in final, the step of the treatment for digestion by trypsin is carried out in a state that the amino group on lysine residue side chain is protected with N-acylation; which avoids such occurrence of fragmentation into unnecessary large number of fragments, which results from the digestion of peptide chain at the two kinds of cleavage sites, i.e. arginine residue and lysine residue, and thus the long peptide chain can be divided into a plurality of peptide fragments by means of digestion by trypsin at the arginine residues that are contained at appropriate frequency in the peptide chain; as a result, a molecular weight of the resulting C-terminal side peptide fragment can be in a molecular weight range suitable for MALDI-TOF-MS measurement.

In the present invention, desalting treatment is conducted after the digestion treatment by trypsin, the resulting peptide fragments are recovered and dried, and then molecular weights of ion species that are derived from the mixture of the peptide fragments obtained by digestion treatment by trypsin are measured with use of a MALDI-TOF-MS apparatus. Incidentally, as desalting treatment is conducted after the digestion treatment by trypsin, the dried-up peptide fragments recovered are by no means fragments forming variety of salt forms but are peptide fragments per se. In the ionization stage thereof, there are generated a cationic species formed by addition with a proton ($H^+$) and an anionic species formed by detachment of proton ($H^+$); and these cationic species and anionic species are separately measured by selecting the detection mode. In the present invention, of the peptide fragments produced by digestion by trypsin, in a series of peptide fragments derived from the N-terminal side amino acid sequence that is common to the original peptide and the reaction products resulting from successive release of C-terminal amino acids, an arginine residue having a guanidino group with high proton ($H^+$) acceptability is present at the fragment C-terminus, which conduces to stabilization of a cationic species with addition of a proton ($H^+$). On the other hand, in the C-terminal side peptide fragments, such an arginine residue is not present, and thus there occurs no stabilization of a cationic species with addition of a proton ($H^+$) that is due to the presence of arginine residue. In connection with this difference, in the mass spectra for cationic species measured by the MALDI-TOF-MS apparatus, the peak intensities that are attributed to a series of peptide fragments derived from the common N-terminal side amino acid sequence, which have an arginine residue at the fragment C-termini thereof, are relatively high. Meanwhile, in the C-terminal side peptide fragments wherein no arginine residue is present, a carboxy group (—COOH) having proton ($H^+$) donatability is present at the C-terminus thereof, and thus in the mass spectra for anionic species measured by the MALDI-TOF-MS apparatus, the peak intensities that are attributed to the C-terminal side peptide fragments are relatively high.

In the present invention, the desalted and dried peptide fragments are subjected to measurement by MALDI-TOF-MS apparatus, and then the mass spectra for cationic species and for anionic species are compared with each other to find out the aforementioned differences in relative intensities therebetween; and by using the differences in relative intensities, there can be discriminated the peaks that are originated from the series of peptide fragments each having an arginine residue at the fragment C-terminus, which are derived from the common N-terminal side amino acid sequence, and further in the mass spectra for the anionic species, there can be easily distinguished the peaks that are originated from the series of the C-terminal side peptide fragments, which are ascribed to community in the N-terminal side amino acid sequence between the original peptide and the reaction products produced by the successive release of C-terminal amino acids.

In said molecular weight measurements for anionic species, there are measured the decreases in molecular weight associated with the successive release of C-terminal amino acids, based on a series of peaks each having a higher intensity, whereby the assignment of each amino acid giving a corresponding molecular weight change is determined. Incidentally, each of the C-terminal side peptide fragments each having no arginine residue, formed by digestion by trypsin has an α-position amino group (—$NH_2$) at the N-terminal amino acid residue and, therefore, shows a corresponding peak also in the mass spectra of cationic species; hence, the result of assignment of each amino acid can be reconfirmed by utilizing the molecular weight of the corresponding peak observed in the mass spectra of cationic species.

More detailed description is made below on each of the method for analysis of C-terminal amino acids of peptide according to the first aspect of the present invention and the method for analysis of C-terminal amino acids of peptide according to the second aspect of the present invention.

In the method for analysis of C-terminal amino acids of peptide according to the first aspect of the present invention, first, an isolated dry sample of peptide is subjected to the following treatment, in the step of subjecting a target peptide to a chemical means to successively release the C-terminal amino acids of the peptide to prepare a mixture containing a series of reaction products [this step is the steps (1) to (3) of the previously-mentioned steps (1) to (6) characterizing the present invention].

Prior to the step of successively releasing the C-terminal amino acids of target peptide, there is carried out a pretreatment (N-acylation protection) step of applying N-acylation by the acyl group of the above-mentioned alkanoic acid anhydride, to the N-terminal amino group of the peptide as well as to the side chain amino group of the lysine residue which may be contained in the peptide. The N-acylation protection to the side chain amino group of lysine residue, applied in the pretreatment step is carried out in order to prevent the cleavage in the C-terminal side peptide bond of lysine residue which occurs in the digestion by trypsin conducted finally; therefore, it is desired to select such an acyl group that the N-acylation protection on the side chain of lysine residue is not deprotected in the hydrolysis treatment described later but the O-acylation protection made simultaneously therewith is deprotected sufficiently. Therefore, in the first aspect of the present invention, there is used, as a reaction reagent which is supplied as a vapor and which can apply N-acylation protection and O-acylation protection to a dry sample of peptide, a combination of an alkanoic acid anhydride (which is an electrophilic acylating agent) and an alkanoic acid (which acts as a catalyst for promotion of acylation, owing to the proton donability).

The alkanoic acid anhydride and alkanoic acid used in the pretreatment step are allowed to act on the peptide chain in a dry atmosphere as a vapor having a particular partial pressure ratio; therefore, they are vaporized from a mixture of the alkanoic acid anhydride and a small amount of the alkanoic acid, in a air-tight reaction vessel which is maintained at a temperature selected in a range of 10 to 60° C. It is preferred to use a mixture capable of giving a desired partial pressure ratio at a temperature selected in a range of 10 to 60° C., specifically an alkanoic acid of 2 to 4 carbon atoms and a symmetric anhydride of said alkanoic acid of 2 to 4 carbon atoms. It is more preferred to use a linear-chain alkanoic acid of 2 to 4 carbon atoms and a symmetric anhydride of said linear-chain alkanoic acid of 2 to 4 carbon atoms. When the alkanoic acid anhydride and the alkanoic acid added in a small amount are the same kind, there is no case that different alkanoyl groups are present in the N-alkanoylation protection and O-alkanoylation protection achieved, even if an acyl exchange reaction has taken place in the course of N-alkanoylation and O-alkanoylation. Therefore, even when part of the O-alkanoylation protection remains protected in the hydrolysis treatment described later, the difference in molecular weight between deprotected molecule and protected molecule is known beforehand and the peak of the protected molecule can be identified easily. In the pretreatment step of applying N-acylation protection, it is ordinarily desired to use a combination of acetic anhydride and acetic acid.

Specifically explaining, in the pretreatment step of applying N-acylation protection, an alkanoic acid anhydride and an alkanoic acid are allowed to act on a dry sample of peptide in a vapor state; therefore, in order to obtain an appropriate vapor pressure, it is preferred that the alkanoic acid anhydride used in the pretreatment step is the same as the alkanoic acid anhydride used in the subsequent step of successively releasing C-terminal amino acids. This alkanoic acid anhydride has, in a dry atmosphere at a temperature selected in a range of 10 to 60° C., a reactivity too low to cause a side reaction such as cleavage of peptide; in the pretreatment step, the catalysis of the alkanoic acid used together with the alkanoic acid anhydride is far inferior to that of perfluoroalkanoic acid; therefore, N-acylation protection can be carried out without causing undesired side reactions.

when a peptide of long amino acid sequence, such as protein has a secondary structure or a tertiary structure, a defolding treatment is beforehand applied to convert the structure into a peptide chain which does not show such a higher order structure; thereby, N-acylation protection proceeds even to all the side chain amino groups of lysine residue present in the peptide, under the condition of applying N-acylation protection to the N-terminal amino group of the peptide. Further, O-acylation protection proceeds to the side chain hydroxy groups of serine residue and threonine residue present in the peptide, and these groups are protected. Furthermore, the side chain phenolic hydroxy group of tyrosine residue present in the peptide undergoes O-acylation partially although the reactivity differs. As a result of the pretreatment step where these plurality of acylation protections are made, all of the side chain amino group of lysine residue and the side chain hydroxy groups of serine residue and threonine residue undergo protection (modification) and the resulting groups are no longer able to take part in undesired side reactions.

Incidentally, there is substantially no fear that the combination of an alkanoic acid anhydride and an alkanoic acid, used in the pretreatment step causes undesired side reactions such as cleavage of peptide in the middle. However, the temperature of the pretreatment is preferably a temperature selected in a range of 10 to 60° C., more preferably around room temperature or a temperature range slightly higher than room temperature. Specifically, the temperature is preferably selected in a range of 15 to 50° C. The proportion of the alkanoic acid in the mixture of the alkanoic acid anhydride and the alkanoic acid is preferably 2 to 10% by volume, specifically 5% by volume relative to the total volume of the alkanoic acid anhydride and the alkanoic acid.

Incidentally, the speed of N-acylation in the pretreatment step varies depending upon the partial pressures (gas-phase concentrations) of the alkanoic acid anhydride and alkanoic acid used and the temperature of the reaction (N-acylation). Therefore, the reaction time in the pretreatment step is desired to be appropriately selected depending mainly upon the reaction temperature. For example, when the reaction temperature is selected at 50° C., the reaction time is selected within 1 hour, for example, at 30 minutes, whereby N-acylation to the N-terminal amino group of peptide can be completed. At that time, it is preferred to add pyridine of catalytic amount, for example, 0.1 to 1.0% by volume relative to the total of the alkanoic acid anhydride and the alkanoic acid, in order to promote the acylation by the alkanoic acid anhydride and the alkanoic acid. This pyridine base, which functions as a proton acceptor, allows, for example, easier removal of the proton to be detached in association with the acylation of amino group.

When the target peptide forms, for example, a —S—S— bond of oxidized type with the cysteine of an adjacent peptide molecule or per se contains cysteine having a —S—S— bond, an ordinary reducing treatment is applied beforehand to remove such a bridge for conversion into a peptide containing cysteine of reduced type. When cysteine of reduced type is present in the target peptide, carboxymethylation, pyridylethylation or the like is applied to the side chain sulfanyl group (—SH) of the cysteine for protection thereof. Specifically explaining, when the target peptide is a peptide of long amino acid sequence, such as protein and has a secondary or tertiary structure and when its molecule may contain cysteine having a —S—S— bond, an ordinary reducing treatment is applied in the stage of applying a defolding treatment for conversion into a peptide chain not showing such a higher order structure, whereby such a bridge is removed and the original peptide is converted into a peptide containing cysteine of reduced type. In addition, to the cysteine of reduced type present in the original peptide is applied carboxymethylation, pyridylethylation or the like to the side chain sulfanyl group (—SH) of the cysteine for protection thereof.

As the procedure of such a pretreatment step, there can be mentioned a procedure which comprises placing a liquid mixture of an alkanoic acid anhydride and a small amount of an alkanoic acid in a sealable reactor, cooling this mixture once to reduce the vapor pressure thereof, degassing the reactor, and increasing the reactor-inside temperature to a reaction temperature to vaporize the alkanoic acid anhydride in the reactor. By employing such a procedure, there is another advantage that the leakage of water into the reactor can be prevented. Further, by conducting degassing so that no oxygen remains in the reaction system, for example, the sulfur present in methionine, which is included in amino acid residues constituting the target peptide, can be prevented from oxidation by oxygen and subsequent change of its scheme weight. In the method of present invention which is based on the measurement of molecular weights, such prevention of oxidation is preferred for achieving a higher accuracy. After the reaction of the pretreatment step has been over, the reaction reagent remaining in the reactor is removed and then the subsequent step for successively releasing the C-terminal amino acids of the original peptide is conducted.

In the reaction for successive release of the C-terminal amino acids of the original peptide according to the first aspect of the present invention, there are allowed to act, on the dry sample of the peptide after N-acylation protection, an alkanoic acid anhydride and a perfluoroalkanoic acid both of vapor phase and supplied from a mixture of an alkanoic acid anhydride and a small amount of a perfluoroalkanoic acid, in a dry atmosphere at a temperature selected in a range of 15 to 60° C.; and at the C-terminus of the peptide, the C-terminal amino acids are released successively in association with the formation of a 5-oxazolone structure represented by the following general scheme (III):

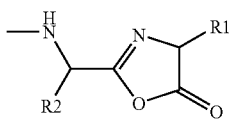

(III)

(wherein R1 is a side chain of the C-terminal amino acid of the peptide and R2 is a side chain of the amino acid residue positioned just before the C-terminal amino acid) and the subsequent cleavage of the 5-oxazolone ring.

In this reaction for formation of 5-oxazolone ring, first, at the state of the keto-enol tautomerism represented by the following reaction scheme (Ia):

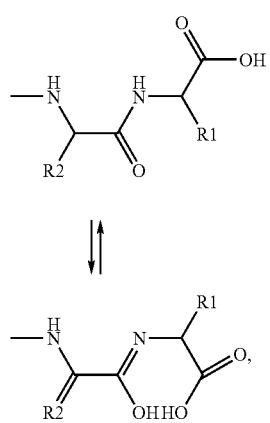

(Ia)

the ratio for staying in the enol state is heightened by allowing the perfluoroalkanoic acid of vapor phase to function as a proton donor toward the dried peptide, in a dry atmosphere.

Then, an intramolecular ester bond is formed, in the enol type, between the exposed hydroxy group and the C-terminal carboxy group to complete the formation of 5-oxazolone ring. It is estimated that, in this esterification reaction as well, the perfluoroalkanoic acid of vapor phase functions probably as a proton donor to induce the esterification reaction proceeding under an acid catalyst. In the first aspect of the present invention, an alkanoic acid anhydride is used as a reagent for activation of C-terminal carboxy group, for conversion into an asymmetric acid anhydride as illustrated by, for example, the following reaction scheme (Ib):

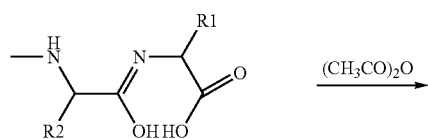

(Ib)

-continued

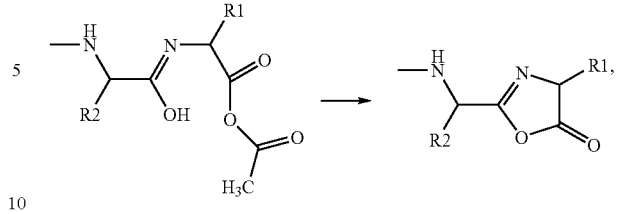

and thus the activated C-terminal carboxy group is involved in the reaction. As a result, such a reaction can proceed under a mild temperature condition and the reaction temperature can be selected in a range of 15° C. to 60° C. Incidentally, such a reaction temperature is selected preferably at around room temperature or in a temperature range slightly higher than room temperature, and more preferably in a specific range of 15° C. to 50° C.

In the treatment using the mixture of an alkanoic acid anhydride and a small amount of a perfluoroalkanoic acid, the alkanoic acid anhydride gives rise ordinarily to N-acylation to the N-terminal amino group of peptide and, therefore, N-acylation protection is achieved in the system; however, it is desired to apply a pretreatment aiming at N-acylation protection.

Thus, in the first aspect of the present invention, the high proton donatability of perfluoroalkanoic acid is utilized, and thus a perfluoroalkanoic acid of which pKa is within a range of 0.3 to 2.5 is preferably used. In addition, since this perfluoroalkanoic acid needs to be supplied to a dried peptide sample in a vapor phase, it is preferred that the perfluoroalkanoic acid is superior in volatility so that a desired vapor pressure is obtained at said temperature selected in a range of 15° C. to 60° C. From this standpoint as well, a perfluoroalkanoic acid having 2 to 4 carbon atoms is more suitable, and a linear-chain perfluoroalkanoic acid having 2 to 4 carbon atoms is particularly suitable. Specifically, use of trifluoroacetic acid ($CF_3COOH$), pentafluoropropanoic acid ($CF_3CF_2COOH$) or heptafluorobutanoic acid ($CF_3CF_2CF_2COOH$) is desired.

The alkanoic acid anhydride used as an activation reagent is consumed with the progress of the reaction; therefore, it is desired to conduct the reaction while the vapor pressure of the alkanoic acid anhydride supplied in a vapor phase is maintained at a given level. Examples of the means used for achieving the purpose include such a means that the reaction system is kept in a sealed state and thereby the vapor pressure of the alkanoic acid anhydride present in the system is stabilized. More particularly, exemplified is such a procedure in which a liquid mixture of an alkanoic acid anhydride and a small amount of a perfluoroalkanoic acid is placed in a sealable reactor; the liquid mixture is once cooled to reduce its vapor pressure; in this state, the reactor inside is evacuated and then sealed off; the alkanoic acid anhydride is vaporized in the reactor by heating up to a reaction temperature. By employing such a procedure, there is another advantage that the leakage of water into the reactor can be prevented. Further, when evacuation is conducted so that no oxygen remains in the reaction system, for example, the sulfur present in the methionine, which is included in the amino acid residues composing a target peptide, can be prevented from oxidation by oxygen and consequent change of its formula weight. In the method of the present invention based on the measurement of molecular weights, such prevention of oxidation is further preferred for achieving a higher accuracy.

As the alkanoic acid anhydride, variety of alkanoic acid anhydrides are usable as long as they can produce an appropriate vapor pressure when heated to the temperature of reaction. However, there is preferred an alkanoic acid anhydride which gives a sufficient vapor pressure when the reaction temperature is selected in the above-mentioned preferable range, for example, of 15° C. to 50° C. Therefore, a symmetric anhydride of an alkanoic acid having 2 to 4 carbon atoms is used preferably. As the symmetric acid anhydride, a symmetric anhydride of a linear-chain alkanoic acid having 2 to 4 carbon atoms is used more preferably, and a symmetric anhydride of a linear-chain alkanoic acid having 2 carbon atoms, i.e. acetic anhydride is used particularly preferably. Since such an alkanoic acid anhydride is used for the activation of C-terminal carboxy group, the anhydride is preferred to give minimum steric hindrance, and the above-mentioned acetic anhydride, etc. are very suitable in this respect as well.

The alkanoic acid anhydride and perfluoroalkanoic acid used in the successive release of C-terminal amino acids are allowed to act on a dried peptide sample in respective vapor states. The reaction is conducted in a dry atmosphere in order to avoid the hydrolysis of once-formed 5-oxazolone ring by the water incoming from outside of the system and its reversion to original structure. In this view, it is more desirable that the reaction is carried out generally in a sealed reactor. Incidentally, the mixture of the alkanoic acid anhydride and the perfluoroalkanoic acid, initially fed into the reactor is, at room temperature, a liquid mixture wherein the alkanoic acid anhydride and the perfluoroalkanoic acid are mixed uniformly. In this mixture containing the alkanoic acid anhydride and a small amount of the perfluoroalkanoic acid, the perfluoroalkanoic acid functioning as a catalyst is not consumed during the reaction in principle and therefore its content can be a small amount. Specifically explaining, the vapor of perfluoroalkanoic acid present in the vapor phase, as compared with the vapor of alkanoic acid anhydride co-existing, can be in a relatively low concentration. In other words, depending upon the kinds of the alkanoic acid anhydride and perfluoroalkanoic acid used, for instance, upon the respective saturated vapor pressures thereof at the reaction temperature, there is appropriately selected a liquid mixture having a mixing ratio which can achieve an intended partial pressure ration (a concentration ratio in vapor phase). The content of perfluoroalkanoic acid in the mixture of the alkanoic acid anhydride and a small amount f the perfluoroalkanoic acid, is desired to be selected, for example, in a range of 1 to 20% by volume, preferably in a range of 3 to 10% by volume relative to the total volume of the alkanoic acid anhydride and the perfluoroalkanoic acid.

In the first aspect of the present invention, it is judged that, from the once-formed 5-oxazolone ring, the separation of the C-terminal amino acid and the formation of the reaction intermediate for the next stage proceed, for instance, via such a reaction as shown by the following reaction scheme (II'):

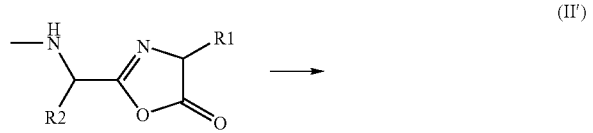

(II')

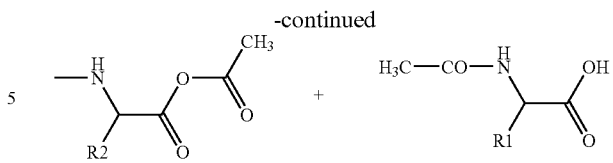

as a result, successive release of C-terminal amino acids is advanced. Therefore, the reaction products obtained after the completion of such reactions are a mixture comprising, in addition to those having a carboxy group exposed at the C-terminus, such as shown in the above reaction scheme (II), an intermediate product having the 5-oxazolone ring structure and a form of reaction intermediate in which its C-terminus has been converted into the form of asymmetric acid anhydride.

The reaction occurring in the step of successively releasing the C-terminal amino acids of peptide comprises at least two-stage elementary reactions, i.e. a stage of formation of 5-oxazolone ring structure as illustrated by the reaction scheme (Ib) and a stage of separation of C-terminal amino acid by the cleavage of 5-oxazolone ring structure, as illustrated by the reaction scheme (II'). Therefore, the overall reaction rate depends upon the reaction rates of the two stages, but depends mainly upon the partial pressures (concentrations in vapor phase) of the alkanoic acid anhydride and perfluoroalkanoic acid used as well as on the reaction temperature. In addition, since a series of reaction products are formed by successive reactions, the maximum length of C-terminal amino acid sequence removed by such successive reactions becomes longer as the treatment duration becomes longer. Hence, the treatment duration for the step of selectively releasing C-terminal amino acid in such a successive manner needs to be appropriately chosen depending mainly upon the partial pressures (concentrations in vapor phase) of the alkanoic acid anhydride and perfluoroalkanoic acid used and the reaction temperature employed and also in view of the intended length of the C-terminal amino acid sequence to be analyzed.

There is arranged a hydrolysis step as a post-treatment step in order to convert the forms of reaction intermediates each having no carboxy group exposed at the C-terminus, such as illustrated in the above reaction scheme (II'), formed in the step of successively releasing the selected C-terminal amino acids of peptide, into a form having a carboxy group exposed at the C-terminus. That is, in the first aspect of the present invention, in this hydrolysis step, after there have been removed, in a dry state, the alkanoic acid anhydride and perfluoroalkanoic acid remaining in the mixture containing a series of reaction products, obtained by said step of successively releasing the C-terminal amino acids of peptide, there are supplied a basic nitrogen-containing aromatic compound or a tertiary amine compound both of vapor phase and water molecules, from an aqueous solution of the basic nitrogen-containing aromatic compound or the tertiary amine compound; said water molecules are allowed to act on the above-mentioned reaction products in the presence of the basic nitrogen-containing organic compound, whereby are hydrolyzed the ester bond inside the 5-oxazolone ring and the C-terminal asymmetric acid anhydride structure which is one form of the reaction intermediates and each C-terminal amino acid residue is allowed to have a reproduced carboxy group (—COOH). By the action of water molecules in the presence of the basic nitrogen-containing, aromatic compound, there also occurs deprotection at the side chain hydroxy groups of serine residue and threonine residue and the side chain phenolic hydroxy group of tyrosine residue, all of which are present in the peptide chain and to all of which O-acylation has been applied in the pre-treatment step. Meanwhile, the N-acylation protections to the side chain amino group of lysine residue as well as to the N-terminal amino acid group of peptide chain, are not deprotected and remain. After this hydrolysis, there is carried out a redrying post-treatment of removing the basic nitrogen-containing aromatic compound and water molecules remaining in the mixture containing a series of reaction products of hydrolysis and then conducting drying. By applying such hydrolysis, the side chain amino group of lysine residue is N-acylated in the original peptide and the series of reaction product peptides and the respective C-terminal carboxy groups are exposed. In this state, they are subjected to digestion by trypsin.

The basic nitrogen-containing aromatic compound or tertiary amine compound both of vapor phase, used in the hydrolysis has no ability to react with, for example, products having such a form in with its C-terminus has been turned into an asymmetric acid anhydride or to form any amide bond therewith; and further, the basic nitrogen-containing aromatic compound or tertiary amine compound can be made into a uniform solution when made into an aqueous solution and is therefore suitable for use in the hydrolysis. As the basic nitrogen-containing aromatic compound which can be used, there is preferred a monocyclic, nitrogen-containing, aromatic compound which can give an appropriate vapor pressure, and, for example, pyridine can be more suitably used. As the tertiary amine compound which can be used, there is preferred one having the same weak basicity as shown by pyridine and, for instance, DMAE [$(CH_3)_2N—CH_2CH_2OH$] can be suitably used. When for example, pyridine is used, the pyridine content is preferably selected in a range of 5 to 15% by volume, specifically at 10% by volume relative to the whole volume of the aqueous solution thereof. When (dimethylamino)ethanol (DMAE) is used, the DMAE content is preferably selected in a range of 1 to 20% by volume, specifically at 10% by volume relative to the whole volume of the aqueous solution thereof.

The monocyclic nitrogen-containing aromatic compound or tertiary amine compound is allowed to act on a dried mixed sample containing the reaction products, in the vapor state together with water molecules. In this post-treatment as well, the reaction is desired to be conducted generally in a sealed reactor. In said post-treatment, since water molecules are used, their vapor pressure needs to be set at a certain level or higher. Therefore, the treatment temperature is desirably chosen, for example, at a temperature of 60° C. or more but, when the mechanical strength of the reactor is taken into consideration, in a range of 100° C. or lower. In order to complete the hydrolysis quickly, a temperature of 100° C. or slightly lower is desired to be selected.

In the selective release of C-terminal amino acids according to the first aspect of the present invention, it is very preferable to carry out the pretreatment step, the step of selectively releasing C-terminal amino acids and the post-treatment step, for example, in the same reactor and continuously. An example of the flow pattern of these steps is illustrated in FIG. 1. A drying-up operation is conducted in said flow when each step has been completed, so that the reagents used in each step do not remain in the peptide sample. This drying-up operation is generally conducted by vacuum distillation, and thereby the C-terminal amino acids released that are by-products in said reaction can be removed as well, in some cases. The flow pattern of steps of FIG. 1 illustrates a case wherein acetic anhydride of high availability in a very high purity is utilized as the alkanoic acid anhydride used therein.

On the other hand, in the flow pattern of steps illustrated in FIG. 1, as for the treatment duration in the step of selectively releasing C-terminal amino acids, there is shown a range of treatment time which is selected depending upon the proportions of the acetic anhydride and perfluoroalkanoic acid used and the treatment temperature employed, for a model case where the length of amino acids of the C-terminal amino acid sequence to be truncated in said step is intended to be ten odd amino acids as maximum case and 3 amino acids as minimum case. In general, when the proportion of the perfluoroalkanoic acid is larger and the treatment temperature is higher, the reaction rate is higher, and thereby it is possible to prepare, in a shorter duration, a series of reaction products wherein the intended maximum amount of truncation from amino acid sequence has been attained.

Furthermore, in the pretreatment step, N-acetylation to N-terminal amino group of peptide is carried out by using acetic anhydride and acetic acid both of vapor phase. Even in the case of such combination of acetic anhydride and acetic acid, there is, in some cases, a fear, maybe very small, that the activation reaction to C-terminal carboxy group expressed by the above-shown reaction scheme (Ia) and the side reaction caused thereby are induced. In order to suppress such a side reaction, a small amount of pyridine vapor can be allowed to co-exist to form a weak addition salt between the pyridine base and the C-terminal carboxy group of peptide, which may provide a protection effect against the occurrence of the undesired side reaction. Such an addition salt undergoes easy deprotection by conducting a drying-up operation upon completion of the pretreatment step to distill off the pyridine base under vacuum, and no problem occurs in the next step of selectively releasing C-terminal amino acids. From these standpoints, it is preferred to add, for the formation of addition salt, a small amount of a nitrogen-containing, heterocyclic, aromatic compound which can be easily distilled off under reduced pressure and has a weak basicity, such as pyridine. Further, since the formation of addition salt has a protection function also for the carboxy group on the side chain of amino acid, it can effectively prevent coincidentally even the undesired side reaction that is originated from the carboxy group on the side chain of amino acid.

In the first aspect of the present invention, there are determined the differences in the molecular weight between the series of reaction products prepared by successively releasing C-terminal amino acids and the original peptide, by using the measurement results obtained by mass spectrometry, and there are identified amino acids corresponding to the differences in molecular weight. Therefore, it is generally desired that the original peptide remains in the mixture subjected to the measurement by mass spectrometry, in such an amount as to enable the determination of its molecular weight.

Specifically explaining, the method for analysis of the C-terminal amino acid sequence of peptide, according to the first aspect of the present invention may be applied to such a case where the maximum length analyzed for the C-terminal amino acid sequence is as long as ten and odd amino acids. With respect to the contents of the series of reaction products of which kinds reach, as the maximum case, the number of ten and odd, the content of the minimum content reaction product is desired at least to be not smaller than about $\frac{1}{10}$ of the content of the maximum content reaction product. In addition, the remaining amount of the original peptide as well is desired at least to be not smaller than about $\frac{1}{10}$ of the content of the maximum content reaction product. Meanwhile, the required information of C-terminal amino acid sequence is within 10 amino acids in many cases and, when selecting the treatment time in which about 10 amino acids can be released, the above-mentioned requirements regarding the contents can be satisfied.

Next, with respect to the first aspect of the present invention, more detailed description is made on the steps (4) to (6) of the above-mentioned steps (1) to (6) characterizing the present invention, that is, on the step of analyzing, by mass spectrometry, the differences in molecular weight between the original peptide and said series of reaction products, to determine the decreases in molecular weight occurring in association with the successive release of C-terminal amino acids, as well as on the step of, based on the determined decreases in molecular weight, identifying the series of amino acids released successively and arranging these amino acids from the C-terminus of peptide to obtain the information of C-terminal amino acid sequence.

In the present invention, a MALDI-TOF-MS apparatus is used for the measurement of molecular weights; therefore, molecular weight measurement of high precision is possible even for a peptide of high molecular weight. However, even when there is used a MALDI-TOF-MS apparatus suitable for the measurement of molecules of large molecular weight such as peptide, there is an upper limit as to the molecular weight allowing for effective ionization, and therefore it is desired that the maximum amino acids of a peptide that is possibly subjected to measurement does not exceed 30 to 50 amino acids. In addition, amino acids corresponding are identified based on the measured differences in molecular weight; therefore, in order to distinguish two amino acid residues giving a formula weight difference of 1, such as Asn vs Asp, or Gln vs Glu, from each other at a high precision, the molecular weight of the longest peptide, i.e. the peptide with no release of C-terminal amino acid therefrom that is used as a datum point, is preferably in a range of no more than 4,000, more preferably in a range of no more than 3,000. When reduced to amino acids, it is length is preferably 40 amino acids at longest, more preferably in a range of no more than 30 amino acids.

In the first aspect of the present invention, in order to enable its application to a peptide of long amino acid sequence, which is far longer than the above-mentioned amino acid length, such as protein, a peptide chain is cleaved, prior to mass spectrometry, using trypsin which is a protease having a peptide cleavage ability at specific sites of peptide and showing an excellent enzymatic reaction efficiency; and, using the C-terminal peptide fragments obtained, there are measured the differences in molecular weight between the series of reaction products prepared by successive release of C-terminal amino acids and the original peptide.

In the digestion by trypsin, trypsin is allowed to act on a mixture containing the series of reaction products after hydrolysis and redrying, in a buffer solution; thereby, the peptide chains wherein each N-terminal amino group thereof and each side chain amino group of the lysine residue (which may be present therein) are N-acylated and protected, undergo specific-to-trypsin cleavage. In that case, since the side chain amino group of lysine residue is N-acylated and protected, the C-terminal side peptide bond of N-acylated lysine residue is not cleaved in the middle and the C-terminal side peptide bond of the arginine residue present in each peptide chain is selectively cleaved in the middle.

For example, if cleavage occurs at the lysine residue and also at the arginine residue, the total number of the resulting peptide fragments reaches a considerable number and, as a result, there appears a tendency that the average amino acid length of each fragment becomes short and peaks of a considerable number of peptide fragments concentrate in a narrow molecular weight range. If there is such concentration of peaks of a considerable number of peptide fragments, it is difficult, in some cases, to identify intended C-terminal side peptide fragments. In particular, the C-terminal side peptide fragments derived from the series of reaction products obtained by successive release of C-terminal amino acids are low in content when the number of amino acids eliminated is large and, when there are other peptide fragments adjacent thereto, it becomes a big obstacle, in some cases, for identification of intended C-terminal side peptide fragments. In the present invention, since the C-terminal side peptide bond of each arginine residue present in peptide chain is selectively cleaved in the middle, the total number of the resulting peptide fragments do not become unnecessarily large and, moreover, the amino acid length of each intended C-terminal side peptide fragment can be allowed to be in a range of amino acid number suitable for the above-mentioned measurement by using MALDI-TOF-MS apparatus.

After the digestion by trypsin; desalting is conducted, the above-mentioned buffer solution component is removed; the peptide fragments after the digestion by trypsin are recovered and dried; and the dried mixture containing the recovered peptide fragments after the digestion by trypsin are subjected to molecular weight measurements for the cationic species and anionic species generated by an ionization treatment, with use of MALDI-TOF-MS.

As already described, there is employed, in the present invention, a technique which comprises:

based on the results of the molecular weight measurements for cationic species and anionic species, obtained with use of a MALDI-TOF-MS apparatus, judging that the peaks of the peptide fragments each having an arginine residue at the C-terminus, obtained by digestion by trypsin show a higher intensity in the molecular weight measurement for cationic species than in the molecular weight measurement for anionic species, owing to the arginine residue possessed by each fragment, judging that the peaks of the C-terminal peptide fragments obtained by digestion by trypsin, derived from the original peptide and also from a series of the reaction products produced from successive release of the C-terminal amino acids of the peptide show a higher intensity in the molecular weight measurement for anionic species than in the molecular weight measurement for cationic species, owing to no presence of arginine residue in each fragment, and based on the molecular weights of the anionic species corresponding to a series of C-terminal peptide fragments and showing a higher intensity in the molecular weight measurement for anionic species, measuring the decreases in molecular weight which have occurred in association with the successive release of the C-terminal amino acids of the original peptide.

In the method for analysis of C-terminal amino acid sequence of peptide according to the first aspect of the present invention, the amino acids released successively are identified based on the differences in molecular weight. Therefore, distinction between leusine (Leu) residue and isoleusine (Ile) residue both having the same formula weight is impossible in principle, which is the same as in the conventional method for analysis of C-terminal amino acid sequence using mass spectrometry. Meanwhile, in the present invention, distinction between glutamine (Gln) residue and lysine (Lys) residue (they have the same formula weight) is impossible because the side chain of the lysine (Lys) residue undergoes N-alkanoylation. Further, in the reaction for releasing C-terminal amino acids, conversion of amide bond into enol form and subsequent formation of 5-oxazolone ring structure are essential as shown in the reaction scheme (Ib), and thus no further reaction for release proceeds when cyclic amino acid proline (Pro), in which neither carbonyl group (C=O) nor imino group (—NH—) (they form an amide bond together) is present, has become a C-terminal amino acid. In other words, by confirming that there occurs no further elimination of C-terminal amino acid even when the treatment duration therefor has been prolonged, it is possible to predict that the amino acid residue that is a main factor for such arrest is cyclic amino acid proline (Pro).

Meanwhile, in the present invention, an alkanoic acid anhydride and a perfluoroalkanoic acid are allowed to act in the reaction for subjecting a target peptide to chemical means to successively release the C-terminal amino acids from the peptide to obtain a series of reaction products; therefore, under such reaction condition for successive release of C-terminal amino acids, there proceed O-acylation and N-acylation reaction together to the hydroxy groups present in the serine residue [—NH—CH(CH$_2$OH)—CO—] and threonine residue [—NH—CH(CH(CH$_3$)OH)—CO—] of the peptide, the N-terminal amino group of the peptide, and the ε-position amino group of the lysine residue [—NH—CH(CH$_2$CH$_2$CH$_2$CH$_2$NH$_2$)—CO—] of the peptide, even if no pretreatment step for O-acylation protection and N-acylation protection is applied beforehand to the above groups. As a result, a competitive hindrance effect is obtained against the side reactions (e.g. N,O-acyl rearrangement reaction) caused by the hydroxy groups present in the serine residue [—NH—CH(CH$_2$OH)—CO—] and threonine residue [—NH—CH(CH(CH$_3$)OH)—CO—] of the peptide. In the present invention, however, since the molecular weights of peptide fragments are measured finally, it is necessary to very reliably prevent the in-the-middle cleavage of peptide fragments, caused, for example, by the hydroxy groups present in the serine residue [—NH—CH(CH$_2$OH)—CO—] and threonine residue [—NH—CH(CH(CH$_3$)OH)—CO—] of the peptide, and there is carried out, prior to the step for successive release of C-terminal amino acids, a pretreatment step of applying O-acylation protection and N-acylation protection.

If a number of acetylated forms of serine residue and threonine residue are included in the reaction products obtained finally, the molecular weight differences between such multi-acetylated product and deacetylated product are aligned in the integral times of formula weight 42, specifically 84, 126 and 168, and they are close to the formula weight 87 of serine residue [—NH—CH(CH$_2$OH)—CO—], the formula weight 128 of glutamine residue [—NH—CH(CH$_2$CH$_2$—CONH$_2$)—CO—] or the formula weight 129 of glutamic acid residue [—NH—CH(CH$_2$CH$_2$—COOH)—CO—] and the formula weight 170 of N-acetyllysine residue [—NH—CH(CH$_2$CH$_2$CH$_2$CH$_2$NH—COCH$_3$)—CO—], respectively. Therefore, there is some fear that the peaks for the multi-acetylated products may be mistaken as main peaks and the deacetylated products may be regarded as the above-mentioned amino-acid-eliminated products. In the present invention, a sufficient countermeasure is taken for such fear by selecting, in the post-treatment (hydrolysis) step, conditions in which deprotection of O-acylation protections to serine residue and threonine residue proceeds sufficiently. In addition, since the molecular weight measurement is made after peptide fragmentization, the measurement is conducted in such an analytical precision that the distinction between glutamine residue and glutamic acid residue, which differ in formula weight by only 1, is possible; since the formula weight difference related to the difference in number of remaining acetyl groups differs from the formula weight of an amino acid residue showing a similar formula weight at least with the formula weight difference of 2 to 3, the possibility of the mis-assignment mentioned above is eliminated in many cases.

The reactor vessel is provided with a liquid reagent-holding system that is capable of reserving the liquid reagent for said reaction or each of the liquid reagents combined in the component kit thereof respectively, capable of feeding the liquid reagents for said reactions at given rates to the peptide sample held in said sample container, and capable of maintaining such a state that their direct contact with each other is avoided, and the reactor vessel has a capacity to accommodate said sample container inside. Preferably, the reactor vessel is designed in such a form that the inside can be evacuated; the liquid reagents remaining therein after the completion of the reaction can be distilled off under reduced pressure, and the structure can be made air-tight during the reaction. In addition, the reactor vessel is required to be made of such a material that, when the vapor of the reagent is generated in the reactor vessel, no reaction takes place between the reagent and the wall of the vessel. Therefore, there is suitably used such a vessel formed by using a glass material that is widely used for reactors of chemical reaction. For the cocks used in a sealed-state operation, cocks made of such a material as Teflon® or the like is used suitably.

Successively, more detailed description is made on the method for analysis of C-terminal amino acid sequence of peptide, according to the second aspect of the present invention.

In the second aspect of the present invention, first, there is used a target peptide which has been separated by gel electrophoresis and bound on a gel carrier, in place of the isolated, dried peptide sample used in the first aspect of the present invention. When such a peptide bound on a gel carrier is subjected to a reaction for successive release of the C-terminal amino acids, it is impossible to effectively employ a solid-state reaction using a reaction reagent of vapor phase; therefore, there is employed a technique of infiltrating a reaction agent into the gel carrier to give rise to a liquid-phase reaction. In that case, in the steps (1) to (3) of the above-mentioned steps (1) to (6) characterizing the present invention, i.e. the step of subjecting a target peptide to chemical means to successively release the C-terminal amino acids of the peptide to prepare a mixture containing a series of reaction products, the target peptide is not isolated from the gel carrier and, in that state, the C-terminal amino acids of the peptide are successively released.

That is, in the steps (1) to (3) of the above-mentioned steps (1) to (6) characterizing the present invention, i.e. the step of subjecting a target peptide to chemical means to successively release the C-terminal amino acids of the peptide, there are conducted:

a step of treatment for dehydration of gel carrier, in which the water included in a gel carrier is removed by dilution with a polar aprotic solvent which does not dissolve the gel and has affinity to water in order to eliminate beforehand the water that is an obstacle to the next-stage pretreatment step of carrying out acylation reaction as for a sample o target peptide bound on the gel carrier which is beforehand isolated by electrophoresis, a pretreatment step of applying acylation protection described below, a step of successively releasing the C-terminal amino acids of peptide, and a post-treatment step of applying hydrolysis to the reaction products obtained.

Incidentally, with respect to the gel substance used for peptide separation by gel electrophoresis, there are appropriately selected the conditions under which a plurality of different peptides falling in a particular molecular weight range can give respective spots (or bands) separated from each other, specifically, the sizes of the fine pores formed inside the gel by selecting the proportion of a polyacrylamide in the gel. As a result, there are present, in the spots (or bands) separated from each other, peptides different in electrophoresis speed owing to the differences in peptide chain molecular weight and electric charge amount on surface, in, for example, the SDS-PAGE method. Such peptides are held inside the fine pores formed in the gel; when only the water in the gel is diluted and dissolved by a polar aprotic solvent which does not dissolve the gel but has affinity to water, the peptides can remain bound on the gel carrier at the spots (or bands) separated from each other, even after such dehydration. That is, the polar aprotic solvent used in the dehydration is generally inferior to water in the affinity to the gel substance such as polyacrylamide; therefore, the volume of the gel decrease with the removal of the water which has maintained the sizes of the fine pores of gel and has had solvation with the pore surfaces. As preferable polar aprotic solvents used in the dehydration, there can be mentioned, for example, nitriles having 4 or less carbon atoms, such as acetonitrile ($CH_3CN$) and ketones having 4 or less carbon atoms, such as acetone, when there is used, for example, a polyacrylamide gel. These polar aprotic solvents used in the dehydration are more volatile than water and, when vaporized to dry-up, the gel decreases its volume, becoming a shrunk gel carrier.

In the second aspect of the present invention, in the pre-treatment step of applying acylation protection to peptide chain, the gel carrier loading the peptide thereon is, after the above-mentioned dehydration, immersed in a solution of an alkanoic acid anhydride dissolved in a dipolar aprotic solvent capable of infiltrating into the gel substance and maintaining it in a swollen state, at a temperature selected in a range of 30° C. to 80° C.; thereby, the alkanoic acid anhydride is allowed to act on the target peptide sample bound on the gel carrier, to apply N-acylation protection by the acyl group derived from the alkanoic acid constituting said alkanoic acid anhydride, to the N-terminal amino group of the peptide as well as to the side chain amino group of the lysine residue which may be present in the peptide. This N-acylation protection to the side chain amino group of lysine residue, applied in the pretreatment step has an object of preventing, in the final digestion by trypsin, the in-the-middle cleavage of the C-terminal side peptide bond of lysine residue; therefore, it is desired to select such an acyl group that, in the hydrolysis described later, the N-acylation protection on the side chain of lysine residue is not deprotected but the deprotection of O-acylation protection proceeds sufficiently. In this case, in the second aspect of the present invention, the alkanoic acid anhydride, which is an electrophilic acylating agent, is depolarized inside the molecule in a dipolar aprotic solvent, owing to the action of the solvent; when the acylating agent is allowed to act on a peptide, there proceed N-acylation and O-acylation to amino group and hydroxy group. When an alkanoic acid derived from said alkanoic acid anhydride is by-produced, such N-acylation and O-acylation are promoted by the catalysis of the alkanoic acid. That is, in the second aspect of the present invention, since the alkanoic acid by-produced in the gel carrier does not diffused or dissipated quickly, such an alkanoic acid remaining in the gel carrier can be utilized as a catalyst for promotion of reaction; therefore, an alkanoic acid anhydride alone is used as a reaction agent.

As the alkanoic acid anhydride used in the pre-treatment step, there is preferred an alkanoic acid anhydride capable of achieving N-acylation protection to the side chain amino group of lysine residue at a temperature selected in a range of 30° C. to 80° C., specifically a symmetric anhydride derived from an alkanoic acid having 2 to 4 carbon atoms. Particularly preferred is a symmetric anhydride derived from a linear-chain alkanoic acid having 2 to 4 carbon atoms. When a symmetric alkanoic acid anhydride is used, an alkanoic acid of the same kind is formed as a by-product; therefore, there is no case that different alkanoyl groups are present in the N-alkanoylation protection and O-alkanoylation protection achieved, even if an acyl group exchange reaction has taken place in the course of N-alkanoylation and O-alkanoylation. Therefore, even when part of the O-alkanoylation protection remains protected in the hydrolysis treatment described later, the difference in molecular weight between deprotected molecule and protected molecule is known beforehand and the peak of the protected molecule can be identified easily. In the pretreatment step of applying N-acylation protection, it is ordinarily desired to use acetic anhydride.

In the dipolar aprotic solvent, the alkanoic acid anhydride gives rise to intramolecular polarization and acts as an electrophilic reaction reagent on said amino group of peptide; as a result, the N-acylation proceeds sufficiently even at a temperature of 30° C. or higher. The N-acylation temperature is preferably selected ordinarily at 50° C. or above for promotion of the reaction; however, since the reaction is carried out generally in a closed reactor, the reaction temperature is desirably selected at 100° C. or below in view of the mechanical strength of the reactor. An alkanoic acid is formed in association with the N-acylation; however its amount is slight and the side reaction caused by such an alkanoic acid having a proton donability and the alkanoic acid anhydride present together invites no problem ordinarily in the above-mentioned temperature range. Specifically explaining, the alkanoic acid formed in the reaction system is far inferior in acid catalysis to, for example, perfluoroalkanoic acids and, moreover, its amount is small; therefore, at the above-mentioned temperature condition, there is, as a side reaction, no formation of 5-oxazolone ring structure which is a main reaction in the step of successive release of C-terminal amino acids using a per-fluoroalkanoic acid and an alkanoic acid anhydride. Further, in the pre-treatment step using an alkanoic acid anhydride alone, various side reactions, such as in-the-middle cleavage of peptide main chain bond (—CONH—), which are suppressed even in the step of successive release of C-terminal amino acids using a perfluoroalkanoic acid and an alkanoic acid anhydride, are suppressed to an even lower extent.

Meanwhile, the dipolar aprotic solvent, which gives rise to reswelling of gel, is preferably an organic solvent which can infiltrate into the gel substance and maintain it in a swollen state, has a relatively small molecular size, and has high affinity to the gel substance. In addition, the solvent is preferred to have such a high bipolarity as to allow the alkanoic acid anhydride to cause intramolecular polarization in the above-mentioned N-alkanoylation and O-alkanoylation and have excellent solvency toward an alkanoic acid formed as a by-product. A dipolar aprotic solvent low in vaporization at the above-mentioned reaction temperature is more preferred. For example, formamide ($HCONH_2$) satisfies all the requirements mentioned above, when a polyacrylamide gel is used.

When a given reaction time has passed, the alkanoic acid anhydride in the gel carrier is removed for termination of the reaction. Therefore, the whole gel carrier is washed using a polar aprotic solvent which gives rise to no dissolution of the gel substance and shows affinity to the alkanoic acid anhydride and the dipolar aprotic solvent. That is, by washing with the polar aprotic solvent, there are diluted and removed, by diffusion, the alkanoic acid anhydride and dipolar aprotic solvent which are present in the gel carrier by infiltration. As the polar aprotic solvent satisfying the requirements for the above washing, there can be mentioned, for example, nitrites having 4 or less carbon atoms, such as acetonitrile ($CH_3CN$) and ketones having 4 or less carbon atoms, such as acetone, when a polyacrylamide gel is used. As the polar aprotic solvent used for dilution and washing, there is ordinarily preferred the polar aprotic solvent used in the above-mentioned dehydration step. Further, the polar aprotic solvent used in such washing is more volatile than water; when it is vaporized, the gel is dried, reduces its volume, and becomes a shrunk gel carrier.

In the step of successive release of C-terminal amino acids in the second aspect of the present invention, the reaction is initiated ordinarily by infiltrating a reaction reagent solution into the shrunk gel carrier free of water. Therefore, after the pre-treatment step of N-acylation protection, the gel carrier having a peptide sample bound thereon is immersed, at a temperature selected in a range of 30° C. to 80° C., in a mixed solution obtained by dissolving an alkanoic acid anhydride and a small amount of a perfluoroalkanoic acid in a dipolar aprotic solvent infiltratable into the gel substance and capable of maintaining it in a swollen state, to allow the alkanoic acid anhydride and perfluoroalkanoic acid to act on the peptide sample bound on the gel carrier; at the C-terminus of the peptide, there arises successive release of the C-terminal amino acids of the peptide in association with formation of the 5-oxazolone structure represented by the following general formula (III):

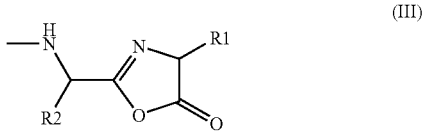

(III)

wherein R1 is a side chain of the C-terminal amino acid of the peptide and R2 is a side chain of the amino acid residue positioned just before said C-terminal amino acid, and subsequent cleavage of the 5-oxazolone ring.

In the reaction for formation of 5-oxazolone ring using a perfluoroalkanoic acid and an alkanoic acid anhydride, first, the perfluoroalkanoic acid is allowed to act as a proton donor on the peptide chain bound in the pores of the gel carrier, in the stage of keto-enol tautomerism represented by the following reaction scheme (Ia):

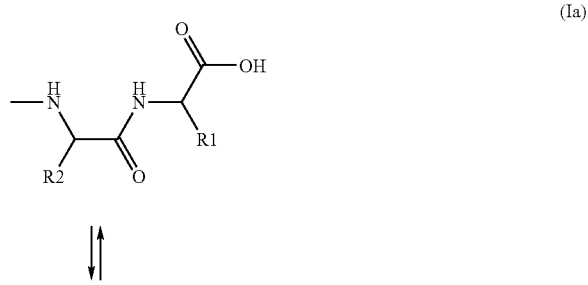

(Ia)

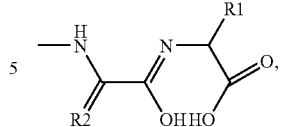

-continued and thereby the ratio of enol form is heightened.

Then, to the enol form is allowed to act the alkanoic acid anhydride as a reagent capable of activating the C-terminal carboxy group of the enol form; thereby, the C-terminal carboxy group is converted into, for example, an asymmetric acid anhydride such as represented by the following reaction scheme (Ib):

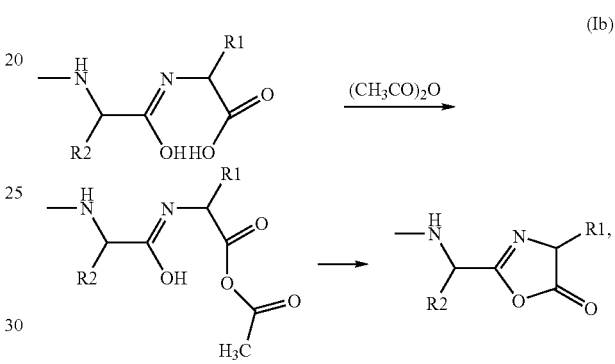

(Ib)

thus, for example, the reaction between the activated C-terminal carboxy group and the hydroxy group of enol form is involved in promotion of the formation of 5-oxazolone ring. In the dipolar aprotic solvent, the alkanoic acid anhydride is contained in a higher concentration than the perfluoroalkanoic acid; thereby, the above reaction can proceed under a mild temperature condition and the reaction temperature can be selected in a range of 30° C. to 80° C.

Meanwhile, in the second aspect of the present invention as well, the catalysis of the perfluoroalkanoic acid is brought about by its proton donatability. As the perfluoroalkanoic acid, there is preferred a perfluoroalkanoic acid whose pKa is in a range of 0.3 to 2.5. There is suitably used a perfluoroalkanoic acid having 2 to 4 carbon atoms, dissolvable uniformly in the dipolar aprotic solvent at the above-mentioned reaction temperature. More suitable is a linear-chain perfluoroalkanoic acid having 2 to 4 carbon atoms. Specifically desired are trifluoroacetic acid ($CF_3COOH$), pentafluoropropanoic acid ($CF_3CF_2COOH$) and heptafluorobutanoic acid ($CF_3CF_2CF_2COOH$).

As the alkanoic acid anhydride used for the activation of the C-terminal carboxy group, there is preferred one showing an appropriate reactivity when the reaction temperature has been reached. Therefore, it is preferred to use a symmetric anhydride of an alkanoic acid having 2 to 4 carbon atoms. Use of a symmetric anhydride of a linear-chain alkanoic acid having 2 to 4 carbon atoms is more preferred and, in particular, a symmetric anhydride of a linear-chain alkanoic acid having 2 carbon atoms, i.e. acetic anhydride is suitable. The alkanoic acid anhydride is preferred to further be able to form 5-oxazolone low in steric hindrance, and acetic anhydride is suitable in this respect as well.

The alkanoic acid anhydride used as an activating reagent is consumed with the progress of reaction; therefore, it is desired to dissolve the anhydride beforehand in the dipolar aprotic solvent used for swelling of gel, in a large excess relative to the amount consumed in the reaction with peptide, in order to suppress the reduction in concentration. Specifically, the ratio of alkanoic acid anhydride and perfluoroalkanoic acid in the mixed solution used for swelling of gel is selected desirably in a range of 1 to 20 volumes (perfluoroalkanoic acid) per 100 volumes of alkanoic acid anhydride and that the concentration of alkanoic acid anhydride in dipolar aprotic solvent is selected desirably in a range of 10 to 30% by volume. The reaction time is desired to be appropriately selected dependently upon the reaction temperature and the concentrations of alkanoic acid anhydride and perfluoroalkanoic acid in dipolar aprotic solvent and also in view of the time required for swelling of the gel carrier shrunk in association with the dehydration using a polar aprotic solvent. For example, the time in which a polyacrylamide gel (12.5% by mass) after dehydration using acetonitrile is immersed in a dipolar aprotic solvent such as formamide to achieve the reswelling of the gel carrier, needs to be, for example, about 3 hours at 40° C.; therefore, the overall reaction time is selected so as to be the sum of the above time of gel reswelling and a time required for selective release of intended amino acid residues, i.e. C-terminal amino acids.

Meanwhile, as the dipolar aprotic solvent used for reswelling of gel, there is preferred an organic solvent which can infiltrate into the gel substance and maintain it in a swollen state, has a relative small molecular size, and has excellent affinity to the gel substance. It is further preferred that the solvent shows such a high bipolarity as, in the stage of keto-enol tautomerism represented by the above-mentioned scheme (Ia), the ratio of enol form can be maintained and that the solvent has high solvency toward the alkanoic acid anhydride and perfluoroalkanoic acid (both are solutes) and the alkanoic acid, which is a by-product formed therefrom. A dipolar aprotic solvent low in volatility at the above-mentioned reaction temperature is more preferred. For example, formamide ($HCONH_2$) satisfies all the requirements mentioned above, when a polyacrylamide gel is used.

The dipolar aprotic solvent having high solvency toward the alkanoic acid anhydride and perfluoroalkanoic acid and the alkanoic acid, which is a by-product formed therefrom, can dissolve even water molecules easily. Therefore, in the reaction in the mixed solution containing such a dipolar aprotic solvent, the reaction system is preferably maintained in a dry atmosphere free of water. That is, the C-terminal carboxy group, which has been converted into a reaction intermediate represented by the above scheme (Ib), i.e. an asymmetric acid anhydride and has been activated, undergoes hydrolysis when water molecules come into the reaction system, and returns to the original carboxy group. In order to avoid such a deactivation stage, the reaction system is preferably maintained in a water-removed state.

For example, the sulfur which is present in methionine as one amino acid residue constituting a target peptide, may undergo oxidation by the oxygen incoming into the system and change its formula weight. Prevention of this oxidation by oxygen is preferred in the method of the present invention which is based on the measurement of molecular weights, in order to achieve a higher accuracy.

In order to maintain the reaction system in a dry atmosphere free of not only water and but also oxygen, it is desired, for example, to make the reaction system air-tight for prevention of the incoming of water and oxygen from outside the system and further conduct the addition and discharge of mixed solution in a dried inert gas, for example, a nitrogen atmosphere. Alternatively, it is desired to avoid the oxidation by using a compound containing a reductive sulfanyl group (—SH), such as DTT, which has an anti-oxidation effects.

In the second aspect of the present invention as well, it is judged that, from the once-formed 5-oxazolone ring, the separation of the C-terminal amino acid and the formation of the reaction intermediate for the next stage proceed, for instance, via such a reaction as shown by the following reaction scheme (II'):

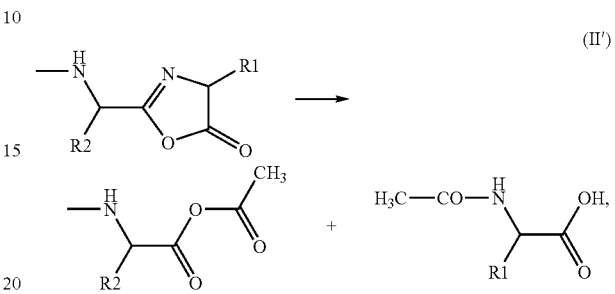

as a result, successive release of C-terminal amino acids is advanced. Therefore, the reaction products obtained after the completion of such reactions are a mixture comprising, in addition to those having a carboxy group exposed at the C-terminus, such as shown in the above reaction scheme (II), an intermediate product having the 5-oxazolone ring structure and a form of reaction intermediate in which its C-terminus has been converted into the form of asymmetric acid anhydride.

The reaction occurring in the step of successively releasing the C-terminal amino acids of peptide comprises at least two-stage elementary reactions, i.e. a stage of formation of 5-oxazolone ring structure as illustrated by the reaction scheme (Ib) and a stage of separation of C-terminal amino acid by the cleavage of 5-oxazolone ring structure, as illustrated by the reaction scheme (II'). Therefore, the overall reaction rate depends upon the reaction rates of the two stages, but depends mainly upon the concentrations of the alkanoic acid anhydride and perfluoroalkanoic acid used as well as on the reaction temperature. In addition, since a series of reaction products are formed by successive reactions, the maximum length of C-terminal amino acid sequence removed by such successive reactions becomes longer as the treatment duration becomes longer. Hence, the treatment duration for the step of selectively releasing C-terminal amino acid in such a successive manner needs to be appropriately chosen depending mainly upon the concentrations of the alkanoic acid anhydride and perfluoroalkanoic acid used and the reaction temperature employed and also in view of the intended length of the C-terminal amino acid sequence to be analyzed.

The termination of the reaction for successive release of selected C-terminal amino acids is conducted by lowering the temperature of the reaction system and diluting and removing the reaction reagent present in the gel carrier, i.e. the perfluoroalkanoic acid and the alkanoic acid anhydride. Specifically explaining, the termination of the reaction and the removal of the reaction reagent are conducted by diluting and removing the mixed solution used for the reaction for successive release of C-terminal amino acids, with a polar aprotic solvent which causes no dissolution of the gel substance and has affinity to the perfluoroalkanoic acid, the alkanoic acid anhydride and the dipolar aprotic solvent. The dilution and removal of the reaction reagent (the perfluoroalkanoic acid and the alkanoic acid anhydride) may be conducted by using the dipolar aprotic solvent used for preparation of the mixed solution. However, for termination of the formation of 5-oxazolone ring structure such as illustrated by the reaction scheme (Ib), it is more desirable to remove the perfluoroalkanoic acid, the alkanoic acid and the dipolar aprotic solvent by using a polar aprotic solvent which hardly contributes to stabilization of enol form intermediate. At least in the final stage of the dilution and removal of the reaction reagent, there is conducted dilution and removal using a polar aprotic solvent. When a polyacrylamide gel is used, there can be mentioned, as the polar aprotic solvent satisfying these conditions, for example, nitrites having 4 or less carbon atoms, such as acetonitrile ($CH_3CN$) and ketones having 4 or less carbon atoms, such as acetone.

In the second aspect of the present invention, the post-treatment of conducting hydrolysis to the series of reaction products obtained by successive release of C-terminal amino acids is carried out as well in a state that the peptide mixture containing the series of reaction products are bound on the gel carrier. That is, the hydrolysis is conducted by immersing the gel carrier loading thereon a mixture containing the series of reaction products obtained by successive release of C-terminal amino acids, in an aqueous solution of a basic nitrogen-containing aromatic compound or a tertiary amine compound, to allow water molecules to act on the reaction product peptides in the presence of the basic nitrogen-containing organic compound.

In this hydrolysis, the basic nitrogen-containing aromatic compound or tertiary amine compound catalyses the hydrolysis of the 5-oxazolone ring structure shown by the reaction scheme (II') and the next-stage reaction intermediate (acid anhydride form); however, the compound per se does not react with the 5-oxazolone ring structure or the reaction intermediate (acid anhydride form) to produce an undesired by-product but functions as an appropriate base catalyst. Specifically explaining, in the hydrolysis of the 5-oxazolone ring structure shown by the reaction scheme (II') and the nextstage reaction intermediate (acid anhydride form), the reaction products have an exposed carboxy group at the C-terminus of peptide chain, as shown in the following reaction scheme (IV).

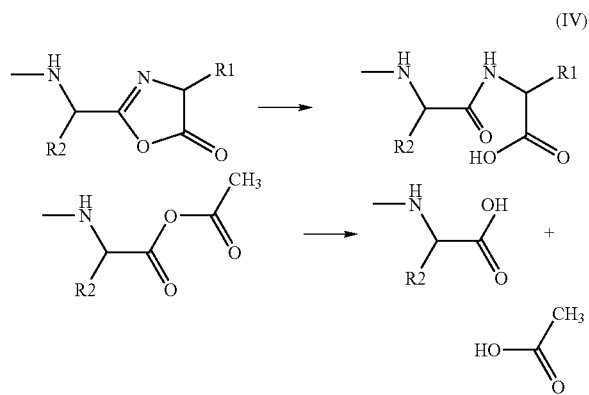

The basic nitrogen-containing aromatic compound or tertiary amine compound used in the hydrolysis is preferred because it does not react with, for example, the reaction intermediate whose C-terminus has been converted into an asymmetric acid anhydride, to form an amide bond and further, when made into an aqueous solution, can become a uniform solution. As the basic nitrogen-containing aromatic compound usable, preferred is a monocyclic, nitrogen-containing, aromatic compound highly soluble in polar aprotic solvents and, for example, pyridine is suitable. As the tertiary amine compound usable, preferred is a compound showing the same relatively weak basicity as pyridine and, for example, DMAE [$(CH_3)_2N\text{—}CH_2CH_2OH$] is suitable. When, for example, pyridine is used, the amount is preferably selected in a range of 5 to 15% by volume relative to the whole volume of the aqueous solution, specifically at 10% by volume. When DMAE [(dimethylamino)ethanol] is used, the amount is preferably selected in a range of 1 to 20% by volume relative to the whole volume of the aqueous solution, specifically at 10% by volume.

The monocyclic, nitrogen-containing, aromatic compound or tertiary amine compound is allowed to act on the gel loading the reaction products thereon, in the form of an aqueous solution. In this post-treatment, the aqueous solution containing such an organic base infiltrates into the highly hydrophilic gel substance quickly. The reaction temperature is selected preferably at 60° C. or above for quick completion of the hydrolysis. However, since the reaction is conducted in a closed reactor, the reaction temperature is desirably selected generally at 100° C. or below, in view of the mechanical strength of the reactor.

The hydrolysis using an aqueous solution containing the organic base is primarily intended to allow a carboxy group to be exposed at the C-terminus of each reaction product peptide chain, and the conditions thereof are selected so that there simultaneously occurs deprotection of the O-acylation protection made in the pre-treatment step but there occurs no deprotection of the N-acylation protections to N-terminal amino group or to the side chain amino group of lysine residue.

Incidentally, when there remains the basic nitrogen-containing aromatic compound or tertiary amine compound used in the hydrolysis, the remaining nitrogen base forms an addition salt with the carboxy group exposed at the C-terminus of each reaction product. Therefore, it is preferred that the aqueous solution present in the gel carrier is diluted and removed using a polar aprotic solvent which causes no dissolution of the gel substance and has affinity to water and, thereby, the gel carrier is redehydrated and the basic nitrogen-containing aromatic compound or tertiary amine compound used in the hydrolysis and the water are diluted and removed. Accordingly, the polar aprotic solvent used in the redehydration is preferably one having high solubility even to the basic nitrogen-containing aromatic compound or tertiary amine compound. When a polyacrylamide gel is used, there can be mentioned, as the polar aprotic solvent for redehydration, satisfying these requirements, for example, nitrites having 4 or less carbon atoms, such as acetonitrile ($CH_3CN$) and ketones having 4 or less carbon atoms, such as acetone.

The hydrolysis conducted after successive release of C-terminal amino acids can be carried out after the dilution and removal of the reaction reagent including the alkanoic acid anhydride and the perfluoroalkanoic acid by using the polar aprotic solvent. Alternatively, the successive release of C-terminal amino acids and the hydrolysis may be carried out continuously. Specifically explaining, when the aqueous solution containing the organic base is added while the temperature of the reaction for successive release of C-terminal amino acids is lowered to terminate the reaction, there occur the deactivation of the reaction reagent, which is a combination of the alkanoic acid anhydride and the perfluoroalkanoic acid, and its dissolution into the aqueous solution from the gel; and there arise the termination of the reaction for successive release of C-terminal amino acids and the deactivation and removal of the reaction reagent. Successively, the hydrolysis of reaction products is made and, by finally applying the redehydration using a polar aprotic solvent, there are conducted removal of the aqueous solution of organic base, the alkanoic acid corresponding to the alkanoic acid anhydride, the perfluoroalkanoic acid and the dipolar aprotic solvent, as well as redehydration; therefore, there is substantially no difference from the case in which the washing and removal operation using a polar aprotic solvent is employed in the middle.

In the step for measuring the decreases in molecular weight occurring in association with the successive release of C-terminal amino acids, according to the second aspect of the present invention, as in the same step of the first aspect of the present invention, as for the dry mixture containing the peptide fragments processed by digestion by trypsin, which are produced by by performing treatment for digestion by trypsin to fragmentize peptide chains of long amino acid length and subsequently recovered, by means of MALDI-TOF-MS, measurement are carried out respectively for the molecular weights of the cationic species and for anionic species, which are both produced by the ionization treatment thereof.

One of the characteristics of the second aspect of the present invention lies in conducting the step of subjecting the above-mentioned mixture containing a series of reaction products after hydrolysis and subsequent redehydration, to digestion by trypsin in a state that the mixture after redehydration is still bound on a gel carrier. Specifically explaining, trypsin dissolved in a buffer solution is allowed to act on the mixture containing a series of reaction products after hydrolysis and subsequent redehyration, in a state that the mixture is still bound on the gel carrier, whereby specific-to-trypsin cleavage is applied to the peptide chains wherein the N-terminal amino group of each peptide chain and the side chain amino group of the lysine group (which may be present in each peptide chain) are protected by N-acylation, and the C-terminal side peptide bond of arginine residue present in each peptide chain is selectively cleaved in the middle and, as a result, peptide fragmentization takes place.

Generally, a gel carrier used for separation of molecular weights by gel electrophoresis such as two-dimensional electrophoresis or SDS-PAGE method is capable of holding peptide chains each having a certain or larger amino acid length, in the gel pores and gives a clear difference in the electrophoresis speeds of the peptide chains; however, when the amino acid lengths of peptide chains are smaller than the above range, the ability of the gel carrier for holding such peptide chains in the gel pores decreases quickly. In the second aspect of the present invention, this uniqueness shown by the gel carrier in gel electrophoresis is utilized; that is, a peptide chain of large amino acid length is subjected to successive release of C-terminal amino acids in a state that the peptide chain has been bound on a gel carrier, to prepare a series of reaction products, then, they are subjected to digestion by trypsin for peptide fragmentization, thereby, intended C-terminal side peptide fragments can be easily detached by dissolution and recovered from the gel carrier.

In the second aspect of the present invention as well, since, in the mixture containing a series of reaction products after hydrolysis, the N-terminal amino group of each peptide chain and the side chain amino group of the lysine group, which may be present in the peptide chain, are protected by N-acylation, there occurs, in the digestion by trypsin, no in-the-middle cleavage of the C-terminal side peptide bond of N-acylated lysine residue but there occurs the selected in-the-middle cleavage of the C-terminal side peptide bond of the arginine residue present in each peptide chain. As explained previously, when there occurs the selected in-the-middle cleavage of the C-terminal side peptide bond of the arginine residue present in each peptide chain, a plurality of peptide fragments are produced from each peptide chain of large amino acid length and, in this case, each of intended C-terminal side peptide fragments generally has such an amino acid length as to correspond to one fraction of the original peptide when divided into several fractions and they are detached form the gel carrier and dissolve in the trypsin solution. Other peptide fragments as well dissolve in the trypsin solution; when the buffer solution and the gel carrier are separated from each other, various peptide fragments detached are recovered in the buffer solution. Then, desalting is conducted, the buffer solution component is removed, and the peptide fragments obtained by digestion by trypsin are recovered and dried.

The later step, that is, the operation from the molecular weight measurements for the dry mixture containing the recovered peptide fragments after digestion by trypsin by, for example, MALDI-TOF-MS, to the determination of C-terminal amino acid sequence based on the results of the above measurements is conducted in the same manner as in the above-mentioned first aspect of the present invention.

As for a protein separated from a sample containing various kinds of proteins, by gel electrophoresis, e.g. two-dimensional electrophoresis or SDS-PAGE method, its rough molecular weight is estimated thereby, and it is composed of a large number of amino acids, in such a case, after the isolation and recovery of such a protein from the spot (or band) separated, there need to be carried out such a series of operations including production of C-terminal side peptide fragments therefrom by using the method according the first aspect of the present invention, measurement of their molecular weights and identification of its C-terminal amino acid sequence based on the results of measurement. The method of the second aspect of the present invention for analysis of C-terminal amino acid sequence of peptide is such method in which, in place of the isolation and recovery of such a protein from the spot (or band) separated, the gel portion containing said spot (or band) is cut out, and the protein is subjected to a series of chemical treatments in a state that the protein is still bound on the gel carrier. In the second aspect of the present invention, the operation of beforehand isolating and recovering a protein from its separated spot (or band) can be omitted and, moreover, the determination of C-terminal amino acid sequence can be carried out at the same accuracy without being affected by the yield in the isolation and recovery.

When there is used the method according to the second aspect of the present invention, the target peptide is made into a linear peptide and subjected to separation by gel electrophoresis to form a single spot bound on a gel carrier. The gel electrophoresis may be a conventional SDS-PAGE method wherein electrophoresis is made in a one-dimensional direction, but may also be a two-dimensional electrophoresis wherein migration is conducted on a gel in a two-dimensional direction for superior separation. With use of such two-dimensional electrophoresis, the separated peptide sample is free from impurities and, even when the sample amount is small, the C-terminal amino acid sequence of the peptide sample can be determined by the method of the second aspect of the present invention. When separation of peptide is made by gel electrophoresis, if the peptide has a —S—S— bond formed between the cysteine residues present in the molecule, it is preferred that there is beforehand added, to the peptide, a reducing reagent such as 2-sulfanylethanol (HS—$C_2H_2$—OH, 2-mercaptoethanol) or DTT (dithiothreitol, threo-1,4-disulfanyl-2,3-butanediol) and electrophoresis is conducted in a reduced state of the peptide to form a single spot. Or, it is preferred to beforehand reduce the —S—S— bond formed between the cysteine residues present in the molecule or to beforehand conduct modification of the reducing type cysteines, such as carboxymethylation using iodoacetic acid or the like, to form a single spot. Thus, by converting the original peptide into a linear peptide free from —S—S— bond formed between the cysteine residues in the molecule, digestion by trypsin can be carried out more efficiently.

EXAMPLES

The present invention is described specifically below by way of Examples. These Examples are examples of the best mode for carrying out the present invention; however, the present invention is in no way restricted by such examples.

Example 1

In order to verify the usefulness of the method for analysis of the C-terminal amino acid sequence of peptide according to the first aspect of the present invention, analysis of C-terminal amino acid sequence was conducted for globin peptide chain, a protein portion of the horse myoglobin which is a heme protein comprising 153 amino acids.

The amino acid sequence possessed by the globin peptide chain of the horse myoglobin, which is a sample to be analyzed in this Example, is already known. Using this sample, the accuracy of the identification for analysis of C-terminal amino acid sequence identified by the analysis method according to the present invention was verified. In FIG. 1 is shown a flow of the process for successive release of C-terminal amino acids, employed in Example 1.

(Preparation of Isolated and Dried Peptide Powder Sample)

First, there is prepared, using a commercially available horse myoglobin standard sample, a peptide solution containing only the globin peptide chain portion thereof at a concentration of 1.0 μg/μl. Said peptide solution is taken into a test tube and lyophilized to prepare a dried peptide powder sample.

(Pre-Treatment Operation)

Next, a vial containing the dried peptide sample is set in a glass-made reactor of air-tight test tube type with fitting stopper, having an evacuation port equipped with a Teflon-made cock valve for sealing. Separately, a given amount of the following liquid reagent is placed in the glass-made reactor. As the reagent for pretreatment, there is used 300 μl of acetic anhydride with 5% by volume of acetic acid added thereto. After the vial containing the dried peptide sample is set in said glass-made reactor, the reactor inside is evacuated under cooling condition and then sealed in an air-tight state.

The whole reactor of air-tight state is kept at 50° C. for 2 hours to allow acetic anhydride and acetic acid both of vapor state, supplied from the liquid reagent in the reactor, to act on the dried peptide sample. By allowing acetic anhydride as an acylation reagent in the presence of acetic acid to act on the dried peptide sample, selective acetylation to the N-terminal amino group of the peptide proceeds. In addition, there take place N-acetylation to the ε-position amino group of the lysine residue (—NH—CH(CH$_2$CH$_2$CH$_2$CH$_2$NH$_2$)—CO—); O-acetylation to the hydroxy groups present in the serine residue (—NH—CH(CH$_2$OH)—CO—) and the threonine reside (—NH—CH(CH$_3$)OH)—CO—); and O-acetylation to the phenolic hydroxy group of the tyrosine residue (—NH—CH(CH$_2$—C$_6$H$_4$—OH)—CO—), which residues are all contained in the peptide chain.

After this pre-treatment is completed, the unreacted acetic anhydride, acetic acid, etc. remaining in the reactor are removed away by distillation under reduced pressure, and the protected and modified globin peptide chain resulting therefrom is dried.

(Operation of Reaction for Release of C-terminal Amino Acids)

Next, in a state that the vial holding the globin peptide chain that is modified and protected with acetyl roup is set in a glass-made reactor of air-tight test tube type with fitting stopper, a given amount of the following liquid reagent is placed anew in the glass-made reactor.

As the liquid reagent for the reaction of selective release of C-terminal amino acids, 300 μl of acetic anhydride with 1% by volume of heptafluorobutanoic acid (HFBA: C$_3$F$_7$COOH) added thereto is used. After the vial containing the dried peptide sample is set in said glass-made reactor, the reactor inside is evacuated under cooling condition and then sealed in an air-tight state.

The whole reactor of air-tight state is kept at 40° C. for 3 hours to allow acetic anhydride and HFBA both of vapor phase, supplied from the liquid reagent in the reactor, to act on the dried peptide sample. Since the HFBA and acetic anhydride are allowed to act on the C-terminus of peptide chain at said heated up temperature, the reactions for successive release of the C-terminal amino acids of peptide chain proceeds via the reaction path of the above-mentioned reaction schemes (Ia) to (II'). In this case, the C-terminus of peptide chain for each reaction product takes a form of the above-mentioned 5-oxazolone ring or a form of an asymmetric acid anhydride whereby activation of carboxy group is accomplished.

After the completion of the treatment for selective release of C-terminal amino acids, the unreacted acetic anhydride, HFBA, etc. remaining in the reactor are distilled off under reduced pressure, and a mixture of the remaining globin peptide chains and the reaction products obtained, which are all protected and modified by acetylaltion, is dried.

(Post-Treatment Operation)

Next, in a state that the vial holding the dried sample of a mixture containing the reaction products is set in a glass-made reactor of air-tight test tube type with fitting stopper, a given amount of the following liquid reagent is placed anew in the glass-made reactor.

As, in the above mixture, the C-termini of reaction product peptides are in a mixture state including those staying in the 5-oxazolone structure, or being advanced even to an asymmetric acid anhydride therefrom, other than those being converted into carboxy group, the post-treatment is a treatment mainly aiming to convert them into a state where all the C-termini of the peptides have turned carboxy groups by applying treatment for hydrolysis to them. That is, an aqueous solution (300 μl) dissolving 10% by volume of DMAE is used as a liquid reagent for post-treatment, and after the vial containing the dried peptide sample is set in said glass-made reactor, the reactor inside is evacuated under cooling condition and then sealed in an air-tight state.

The whole reactor of air-tight state is heated at 60° C. for 1 hour to allow the DMAE and water molecules in vapor phase, supplied from the liquid reagent in the reactor, to act on the dried sample. The asymmetric acid anhydride and the 5-oxazolone structure undergo hydrolysis by the action of water molecules in the presence of DMAE being an organic base, whereby they are converted into a form having a carboxy group at the C-terminus as illustrated in the above-shown reaction scheme (IV). Further, on the peptide chain modified and protected by acetyl group, the protection by O-acetylation to the hydroxy groups present in the serine residue (—NH—CH(CH$_2$OH)—CO—) and the threonine residue (—NH—CH(CH(CH$_3$)OH)—CO—) is hydrolyzed to be deprotected, and the protection by O-acetylation to the phenolic hydroxy group of tyrosine residue (—NH—CH(CH$_2$—C$_6$H$_4$—OH)—CO—) is also hydrolyzed almost completely. However, since the basicity of the organic base used is not high, deprotection of N-acetylation does not proceed and, after the post-treatment, there remain, at a high selectivity, the N-acetylation to N-terminal amino group and the N-acetylation to the ε-position amino group of lysine residue (—NH—CH(CH$_2$CH$_2$CH$_2$CH$_2$NH$_2$)—CO—). In some cases, there only slightly remains the O-acetylation to the phenolic hydroxy group of tyrosine residue (—NH—CH(CH$_2$—C$_6$H$_4$—OH)—CO—).

After such post-treatment, the water molecules, DMAE, etc. remaining in the reactor are distilled off under reduced pressure and the mixture of the reaction products after post-treatment is dried.

(Peptide Fragmentation with use of the Digestion by Trypsin)

The globin peptide chain of horse myoglobin is composed of 153 amino acids and its molecular weight deviates from an appropriate molecular weight range in mass spectrometry; therefore, the treatment for peptide fragmentation by means of the digestion by trypsin is applied to it.

Specifically explaining, the dried sample of a mixture of said reaction products after post-treatment is placed in a container, and an aqueous solution containing trypsin is added to conduct fragmentation of peptide chain. In said aqueous solution containing trypsin, 0.1 μg/μl of trypsin is contained in a 3-pyridine acetate buffer (pH: 7). The enzymatic reaction for the digestion by trypsin is carried out at 37° C. for 8 hours with stirring.

Incidentally, in the original peptide chain and reaction products, the N-acetylation to N-terminal amino group and the N-acetylation to the ε-position amino group of lysine residue (—NH—CH(CH$_2$CH$_2$CH$_2$CH$_2$NH$_2$)—CO—) remain as such even after said deprotection in the post-treatment step; in the digestion by trypsin, the cleavage of the C-terminal side peptide bond of N-acetylated lysine residue does not take place and there progresses only the cleavage of the C-terminal side peptide bond of arginine residue. The amino acid sequence which the globin peptide of horse myoglobin has is already known, and the original peptide chain having 153 amino acids, as shown in FIG. 7, when subjected to the digestion by trypsin at the arginine residues, produces fragments each containing a partial amino acid sequences of 1-31 amino acids, of 32-139 amino acids or of 140-153 amino acids. Therefore, a series of reaction products produced by the above-mentioned successive release of C-terminal amino acids, give a series of mass spectrum peaks reflecting the differences of molecular weights of C-terminal amino acids, together with that of said C-terminal fragment containing a partial amino acid sequence of 140-153 amino acids.

After the digestion by trypsin, the reaction mixture is subjected to desalting using ZipTip and then to separation and recovery of peptide fragments. These peptide fragments are subjected to lyophilization.

(Identification of Reaction Products Processed by Post-Treatment and Peptide Fragmentization by Means of Trypsin Digestion)

The mixture of the reaction products processed by post-treatment and peptide fragmentization by means of trypsin digestion and the C-terminal fragments of globin peptide chain, which are obtained by completion of a series of treatments, is subjected to mass spectrometry to determine the molecular weight of each peptide fragment contained in the mixture.

In this Example, the masses of the main ion species peaks reflecting the molecular weights of individual fragments and the relative peak intensities of the main ion species peaks are measured for the dried sample of peptide fragment mixture by using MALDI-TOF-MS apparatus, and then compared threrebetween. Incidentally, in the measurement by means of MALDI-TOF-MS apparatus, there are conducted two kinds of measurements for separation of ion species, i.e. a negative mode detection wherein negatively charged ion species are introduced into a detector and a positive mode detection wherein positively charged ion species are introduced into a detector. That is, as for the main ion species reflecting the molecular weights of individual peptide fragments, there are obtained two types of spectra corresponding to cationic species raised by proton (H$^+$) addition, in the positive mode detection, and anionic species raised by proton (H$^+$) elimination, in the negative mode detection.

Figure 3:
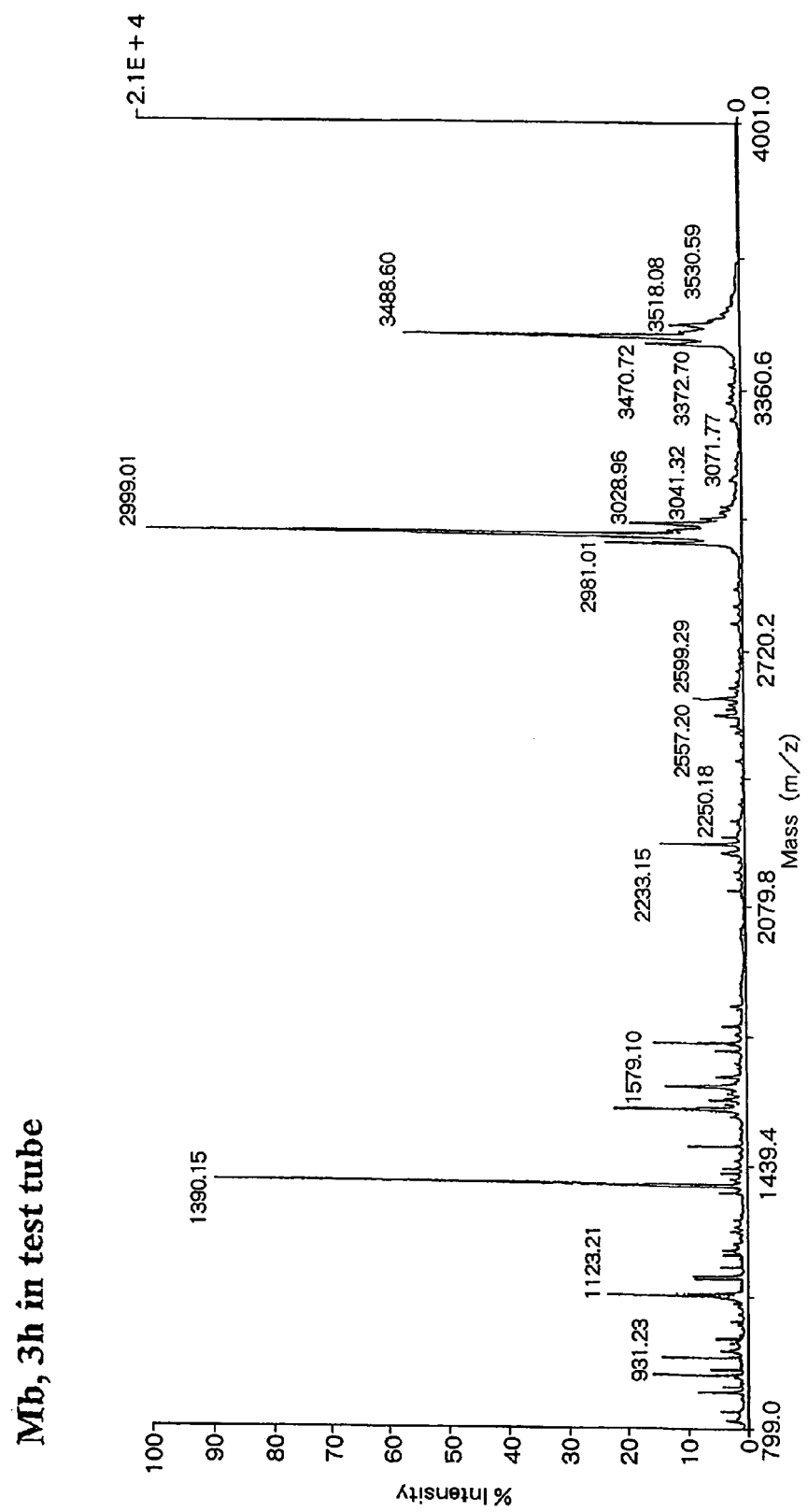
FIG. 3 is a chart showing an example of the mass spectrometry spectrum measured in cationic species detection mode by a MALDI-TOF-MS apparatus for the resulting peptide fragments that are obtained by the treatment process for successive release of C-terminal amino acids from the peptide according to the first aspect of the present invention, in which successive release of C-terminal amino acids of the globin peptide chain was conducted for a dry peptide sample of horse myoglobin, and then the obtained mixture of reaction products was subjected to the digestion by trypsin.
Figure 4:
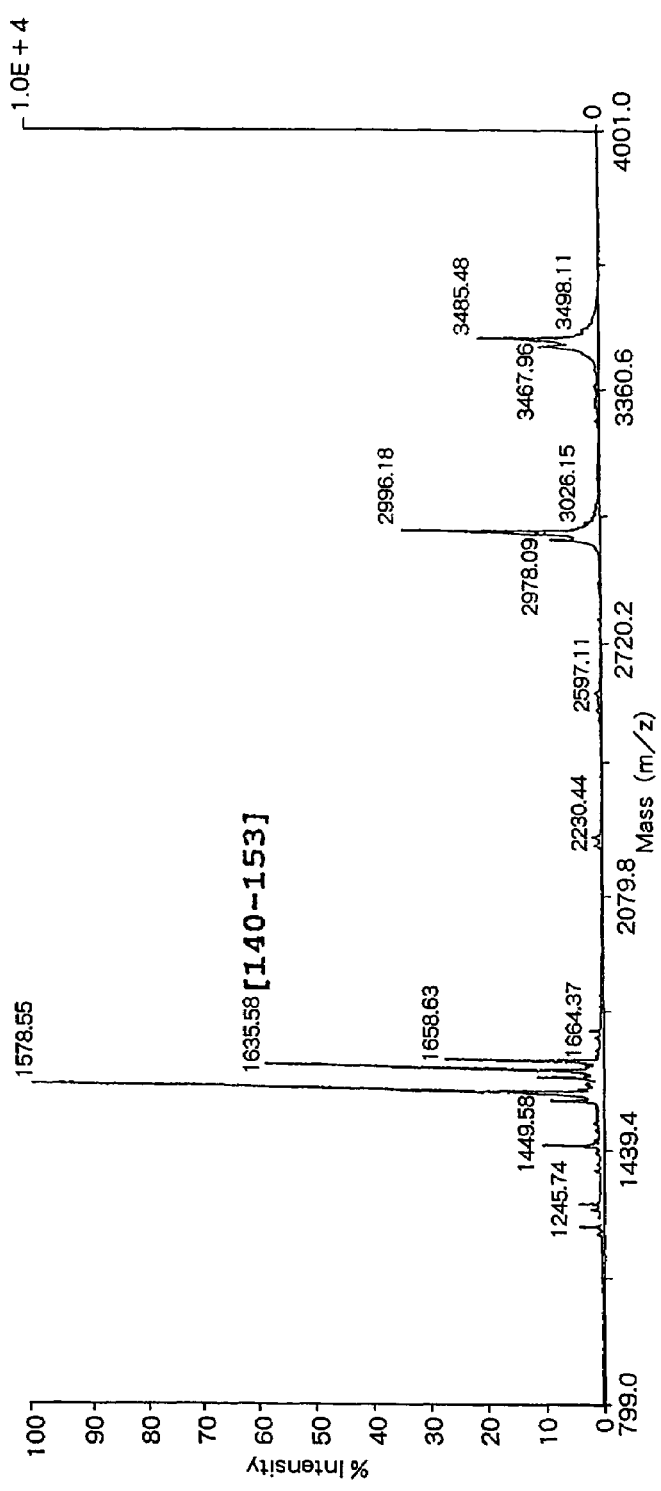
FIG. 4 is a chart showing an example of the mass spectrometry spectrum measured in anionic species detection mode by a MALDI-TOF-MS apparatus for the resulting peptide fragments that are obtained by the treatment process for successive release of C-terminal amino acids from the peptide according to the first aspect of the present invention, in which successive release of C-terminal amino acids of the globin peptide chain was conducted for a dry peptide sample of horse myoglobin, and then the obtained mixture of reaction products was subjected to the digestion by trypsin.

When there are compared the spectrum in the positive mode detection shown in FIG. 3 and the spectrum in the negative mode detection shown in FIG. 4, there are found, as two main peaks corresponding to the fragments due to digestion by trypsin, which are derived from the globin peptide chain of horse myoglobin, fragments each containing a partial amino acid sequence of 1-31 amino acids or a partial amino acid sequence of 140-153 amino acids, in such a molecular weight range. In the positive mode detection shown in FIG. 3, the peak of high relative intensity is judged to correspond to a N-terminal side peptide fragment having a partial amino acid sequence of 1-31 amino acids and having an arginine residue at the C-terminus and, in the negative mode detection shown in FIG. 4, the peak of high relative intensity is judged to correspond to a C-terminal side peptide fragment having a partial amino acid sequence of 140-153 amino acids and containing no arginine residue. There is further found a peptide fragment corresponding to a partial amino acid sequence of 78-102 amino acids, which is derived from partial amino acid sequence of 32-139 amino acids, by cleavage at the N-acetylation-dropped-off lysine residue therein; in the positive mode detection shown in FIG. 3, the intensity thereof exhibits a relatively high peak. Besides, peptide fragments resulting from trypsin autolysis are also found in such a molecular weight range and, in the positive mode detection shown in FIG. 3, their intensities give relatively high peaks as well.

In the negative mode detection shown in FIG. 4, in addition to the C-terminal side peptide fragment of the partial amino acid sequence of 140-153 amino acids, the intensities for a series of C-terminal side peptide fragments derived from reaction products formed by successive release of C-terminal amino acids are also detected to be relatively high. In Table 1 are shown the measured masses of the peaks, their differences from the mass of peak of C-terminal fragment of original globin peptide chain, as well as the amino acids identified therefrom which are removed in individual reaction product fragments and the forms of individual reaction products.

TABLE 1

| m/Z | Δm | Assignment | Corresponding peptide structure |
|---|---|---|---|
| 1636.58 | — | | NDIAAK(Ac)YK(Ac)ELGFGQ |
| 1578.55 | 58.03 | -Gly | NDIAAK(Ac)YK(Ac)ELGFG |
| 1449.58 | 187.00 | -Gln-Gly | NDIAAK(Ac)YK(Ac)ELGF |

TABLE 1-continued

| m/Z | Δm | Assignment | Corresponding peptide structure |
|---|---|---|---|
| 1302.58 | 334.00 | -Phe-Gln-Gly | NDIAAK(Ac)YK(Ac)ELG |
| 1245.74 | 390.84 | -Gly-Phe-Gln-Gly | NDIAAK(Ac)YK(Ac)EL |

By the process for the treatment using a vapor-phase reagent used in the present example 1, a series of reaction products are obtained in which the four amino acids; i.e. glycine, glutamine, phenylalanine and glycine are sequentially eliminated from the C-termini thereof by the treatment for the successive release of C-terminal amino acids. Incidentally, in the negative mode detection shown in FIG. 4 are observed, besides these peaks including that of the C-terminal peptide fragment containing the partial amino acid sequence of 140-153 amino acids described above, two peaks (m.w.: 2996.18, 3485.48) corresponding to peptide fragments of 1-31 amino acid portion and 78-102 amino acid portion, produced by the digestion by trypsin. However, there is not found, in such a molecular weight range, any peptide fragment which can be judged to have been secondarily produced by digestion by trypsin in association with deprotection of lysine residue, other than the fragment of 78-102 amino acid portion. Therefore, by comparing the positive mode detection shown in FIG. 3 with the negative mode detection shown in FIG. 4, there can be easily distinguished the ion species corresponding to the peptide fragments each having an arginine residue at the C-terminus and the peptide fragments each having an N-acetylation-dropped-off lysine residue at the C-terminus, which are both produced by digestion by trypsin. On the other hand, many kinds of peptide fragments caused by digestion by trypsin at lysine residue do not co-exist in such a molecular weight range. Accordingly, when identifying intended C-terminal peptide fragments and a series of C-terminal peptide fragments associated therewith, which are treated for the successive release of C-terminal amino acids, it is easier to conduct such discrimination.

Example 2

In order to verify the usefulness of the method for analysis of the C-terminal amino acid sequence of peptide according to the second aspect of the present invention, analysis of C-terminal amino acid sequence of was conducted for globin peptide chain bound on the gel carrier, which is a protein component of horse myoglobin that is a heme protein comprising 153 amino acids.

In this Example, horse myoglobin, which is used as a sample to be analyzed, was subjected to gel electrophoresis by SDS-PAGE method, using a polyacrylamide gel, to separate the globin peptide chain thereof as a single spot. Then, the accuracy of the identification was verified for its C-terminal amino acid sequence determined by the method of analysis according the present invention.

(Isolation by Gel Electrophoresis)

First, as for a commercially available horse myoglobin standard product, a peptide solution is pepared which contains only the globin peptide chain portion thereof at a concentration of 0.2 μg/μl. Incidentally, the globin peptide chain portion of horse myoglobin contains no cystine residue unlike human myoglobin; however, if there is used a peptide containing cystine residue, like human myoglobin, an anti-oxidation treatment is applied beforehand in order to avoid formation of —S—S— bond due to the oxidation of the sulfanyl group (—SH) of the cystine residue, by, for example, adding a reducing reagent such as 2-sulfanylethanol (HS—$C_2H_2$—OH: 2-mercaptoethanol) or DTT (dithiothreitol: threo-1,4-disulfanyl-2,3-butanediol). If desired, further protection, such as carboxymethylation, for the sulfanyl group (—SH) of the cystine residue is carried out beforehand.

This peptide solution is spotted on a polyacrylamide gel with gel concentration of 12.5% by mass, followed by electrophoresis. Then, Coomassie staining was conducted to identify a band of intended globin peptide chain. In this Example, the stained band portion of gel is cut out and the resulting gel slice is subjected to a series of operations described below.

(Dehydration of Gel)

The gel slice is placed in an air-tight tube; 1 ml of acetonitrile is poured thereinto; stirring is made for 15 minutes. Then, the acetonitrile is discarded; 1 ml of acetonitrile is added newly; stirring is made again for 15 minutes. This extraction treatment of water included in the gel by using acetonitrile is repeated three times in total to complete dehydration treatment of the gel. With the dehydration treatment of the gel, the gel volume contracts.

(Pre-Treatment Operation)

Next, to the dehydrated gel slice in the tube is added 1 ml of a solution containing 10% by volume of acetic anhydride in formamide. The tube that is sealed up tightly in a dry atmosphere, and then the temperature of whole tube is heated up to 50° C. with stirring. It is further held at that temperature for 3 hours.

During this period for keeping in the heated-up condition, the gel in contraction reswells owing to the infiltration of formamide solvent and returns to its original volume. The acetic anhydride solute acts on the globin peptide chain bound on the reswollen gel a t said heated-up temperature. As a result, there proceeds selective acetylation reaction to the N-terminal amino group of the peptide. In addition, there take place coincidentally N-acetylation to the ε-position amino group of the lysine residue (—NH—CH($CH_2CH_2CH_2CH_2NH_2$)—CO—) contained in the peptide chain; O-acetylation to the hydroxy groups present in the serine residue (—NH—CH($CH_2OH$)—CO—) and the threonine reside (—NH—CH($CH_3$)OH)—CO—); and O-acetylation to the phenolic hydroxy group of the tyrosine residue (—NH—CH($CH_2$—$C_6H_4$—OH)—CO—).

After performing the above-mentioned protection with N-acetylation to N-terminal amino group as well as N-acetylation/O-acetylations to side chains of amino acid residues, the solution of acetic anhydride in formamide is removed; 1 ml of acetonitrile is poured into the tube; stirring is conducted for 15 minutes. Then, the acetonitrile is discarded; 1 ml of acetonitrile is added newly; stirring is made again for 15 minutes. This extraction of formamide solution included in the gel by using acetonitrile is conducted three times in total to complete the treatment for removing the solvent (formamide) in the reswollen gel. With the treatment for solvent removal, the gel volume contracts and simultaneously the gel is dehydrated.

(Operation of the Reaction for Release of C-Terminal Amino Acids)

Next, as shown in the process of FIG. 2, there is conducted reswelling of the gel contracted by said dehydration treatment and infiltration of reaction reagent into gel. Specifically explaining, into the tube containing the gel slice, in which the globin peptide chain that is subjected to modification and protection by means of acetylation is kept in a bound state on gel, is poured 1 ml of a solution containing 1% by volume of heptafluorobutanoic acid (HFBA: $C_3F_7COOH$) and 10% by volume of acetic anhydride in formamide. The tube that is sealed up tightly in a dry atmosphere, and then the temperature of whole tube is heated up to 40° C. with stirring. It is further held at the same temperature for 16 hours.

During this period for keeping in the heated-up condition, the gel in contraction reswells owing to the infiltration of formamide solvent and returns to its original volume. HFBA and acetic anhydride act on the C-terminus of the peptide chain bound on the reswollen gel, at said heated-up temperature, whereby the reaction for selective release of C-terminal amino acids of peptide chain proceeds. It is presumed specifically that the reaction of successive release of C-terminal amino acids of peptide chain via formation of 5-oxazolone ring may progress through the stages of reaction shown by the reaction schemes (Ia) to (II') illustrated above. At each of the reaction stages of successive release, reaction is promoted by the catalysis of HFBA, which functions as a proton donor in formamide that is a dipolar solvent.

The reaction for successive release of C-terminal amino acids proceeds in the gel and, as a result, there remains, in a state bound on the gel carrier, a mixture containing a series of reaction products, from which C-terminal amino acids are eliminated stepwisely, and an original peptide chain with modification and protection by acetylation, which is left yet in the stage of converting into the 5-oxazolone structure for the initial step. The formamide solution containing unreacted acetic anhydride, HFBA, etc., remaining in the tube is removed; 1 ml of acetonitrile is poured into the tube; stirring is made for 15 minutes. Then, the acetonitrile is discarded; 1 ml of acetonitrile is poured newly; stirring is conducted again for 15 minutes. This extraction of formamide solution included in the gel by using acetonitrile is carried out three times in total to remove the solvent (formamide) in the reswollen gel. With the treatment for solvent removal, the gel volume contracts and simultaneously the gel is dehydrated.

(Post-Treatment Operation)

Next, into the tube containing a gel slice in a state that the mixture containing the reaction products is bound thereon is poured 1 ml of an aqueous solution containing 10% by volume of DMAE (($CH_3$)$_2$N—$CH_2CH_2OH$). The tube is sealed tightly and then the whole tube is heated up to 60° C., and kept at the temperature for 1 hour with stirring. In this case, the dehydrated gel reswells quickly owing to the infiltration of water solvent and returns to its original volume. Water molecules act, in the presence of the basic nitrogen-containing organic compound and at said heated-up temperature, on the peptide chain and reaction products bound on the reswollen gel, whereby treatment for hydration proceeds.

As, in said mixture, the C-termini of the reaction product peptides are in a mixture state including those staying in the 5-oxazolone structure, or being advanced even to conversion into an asymmetric acid anhydride therefrom, other than those being converted into carboxy group, the treatment for hydration of the post-treatment is a treatment mainly aiming to convert them into a state where all the C-termini of the peptides have turned carboxy groups by applying treatment for hydrolysis to them. Further, since the basic nitrogen-containing organic compound functions as a basic catalyst, there occur, on the peptide chain modified and protected by acetyl group, hydrolysis of the O-acetylation protection to the hydroxy groups present in the serine residue (—NH—CH($CH_2OH$)—CO—) and the threonine residue (—NH—CH(CH($CH_3$)OH)—CO—) to finish deprotection thereof; similarly, hydrolysis of the O-acetylation protection to the phenolic hydroxy group of tyrosine residue (—NH—CH($CH_2$—$C_6H_4$—OH)—CO—) proceeds as well. However, since the basicity of the organic base used is not high, deprotection of N-acetylation protection does not proceed and, after the post-treatment, there remain, at a higher selectivity, the N-acetylation to N-terminal amino group and the N-acetylation to the ε-position amino group of lysine residue (—NH—CH($CH_2CH_2CH_2CH_2NH_2$)—CO—). In some cases, there only slightly remains the O-acetylation to the phenolic hydroxy group of tyrosine residue (—NH—CH($CH_2$—$C_6H_4$—OH)—CO—).

After the end of such post-treatment, the aqueous solution remaining in the tube is removed; 1 ml of acetonitrile is poured into the tube; stirring is made for 15 minutes. Then, the acetonitrile is discarded; 1 ml of acetonitrile is poured newly; stirring is made again for 15 minutes. This extraction of aqueous solution included in the gel by using acetonitrile is conducted three times in total to complete the treatment for dehydration of the reswollen gel. With the treatment for dehydration, the gel volume contracts.

(Fragmentization of Peptide by Digestion with Trypsin)

The globin peptide chain of horse myoglobin is composed of 153 amino acids and its molecular weight deviates from an appropriate molecular weight range in mass spectrometry; therefore, the treatment for peptide fragmentation by means of the digestion by trypsin is applied to it.

Specifically explaining, into the tube containing the gel slice dehydrated by application of said post-treatment is added an aqueous solution containing trypsin and, in a state of peptide chain bound on gel carrier, fragmentation of the peptide chain is carried out. As said aqueous solution containing trypsin is containing trypsin at a concentration of 0.067 μg/μl in an ammonium bicarbonate buffer (pH 8), the enzymatic reaction is performed at 37° C. for 4 hours with stirring to achieve the digestion by trypsin. In this case, the dehydrated gel reswells quickly owing to the infiltration of water solvent and returns to its original volume. At the heated-up temperature, said trypsin, together with the buffer solution, penetrates into the gel and acts on the peptide chain and reaction products bound on the reswollen gel, whereby trypsin-specific enzymatic digestion proceeds.

Incidentally, in the peptide chain and reaction products, the N-acetylation to N-terminal amino group and the N-acetylation to the ε-position amino group of lysine residue (—NH—CH($CH_2CH_2CH_2CH_2NH_2$)—CO—) remain as such even after said deprotection in the step of the post-treatment; in the digestion by trypsin, the cleavage of the C-terminal side peptide bond of the N-acetylated lysine residue does not take place and there proceeds the cleavage of the C-terminal side peptide bond of arginine residue. The amino acid sequence that the globin peptide chain of horse myoglobin has is already known as shown in FIG. 7, and as the result of cleavage of the C-terminal side peptide bond of arginine residue, the original peptide chain composed of 153 amino acids is digested by trypsin into the fragments each containing partial amino acid sequences of 1-31 amino acids, of 32-139 amino acids and of 140-153 amino acids. Incidentally, in FIG. 7, the lysine residues to be protected by N-acetylation in the pretreatment operation are shown in a dotted state; and the partial amino acid sequences of N-terminal side 1-31 amino acids and C-terminal side 140-153 amino acids, which are to be produced by the cleavage of C-terminal side peptide bond of each arginine residue due to the digestion by trypsin, are shown in bold type.

When the fragmentization is made by digestion by trypsin, the peptide fragments are easily eluted from the gel carrier and dissolve away into the trypsin solution in the tube. Incidentally, in the step of the treatment for digestion by trypsin, together with the C-terminal fragment containing a partial amino acid sequence of 140-153 amino acids, the C-terminal fragments that are derived from a series of reaction products formed by the treatment for successive release of C-terminal amino acids dissolve away into the trypsin solution in the tube. Therefore, the digestion treatment by trypsin makes it possible to cleave off the C-terminal portion from the peptide chains of long amino acid length, resulting in the peptide fragments ranging within a desired molecular weight range suitable for mass spectrometry and also makes it possible to elute these peptide fragments away from inside the gel and recover in high yield.

At the end of step of digestion treatment by trypsin, peptide fragments dissolving into the trypsin solution in the tube are recovered from inside the gel. The solution containing a mixture of peptide fragments recovered is subjected to desalting and then lyophilized.

(Identification of Reaction Products Processed by Post-Treatment and Peptide Fragmentization by Means of Trypsin Digestion)

The mixture of the reaction products processed by post-treatment and peptide fragmentization by means of trypsin digestion and the C-terminal fragments of globin peptide chain, which are obtained by completion of a series of treatments, is subjected to mass spectrometry to determine the molecular weight of each peptide fragment contained in the mixture.

In this Example as well, the masses of the main ion species peaks reflecting the molecular weights of individual fragments and the relative peak intensities of the main ion species peaks are measured for the desalted and dried sample of peptide fragment mixture by using MALDI-TOF-MS apparatus, and then compared threrebetween. Incidentally, in the measurement by means of MALDI-TOF-MS apparatus, there are conducted two kinds of measurements for separation of ion species, i.e. a negative mode detection wherein negatively charged ion species are introduced into a detector and a positive mode detection wherein positively charged ion species are introduced into a detector. That is, as for the main ion species reflecting the molecular weights of individual peptide fragments, there are obtained two types of spectra corresponding to cationic species raised by proton ($H^+$) addition, in the positive mode detection, and anionic species raised by proton ($H^+$) elimination, in the negative mode detection.

Figure 5:
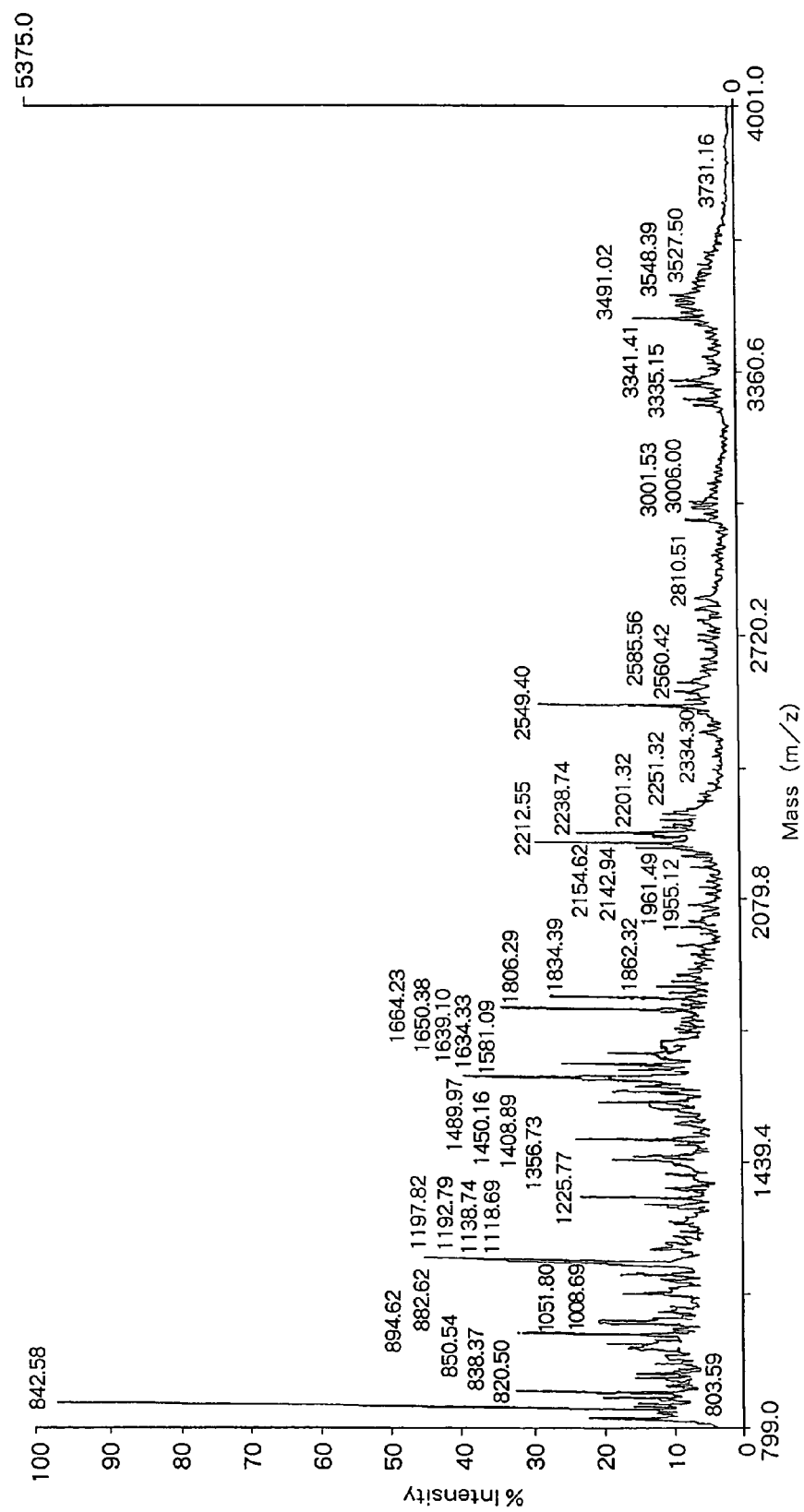
FIG. 5 is a chart showing an example of the mass spectrometry spectrum measured in cationic species detection mode by a MALDI-TOF-MS apparatus for the resulting peptide fragments that are obtained by the treatment process for successive release of C-terminal amino acids from the peptide according to the second aspect of the present invention, in which successive release of C-terminal amino acids of the globin peptide chain was conducted for a sample of horse myoglobin bound on the gel, and then the obtained mixture of reaction products was subjected to the digestion by trypsin.
Figure 6:
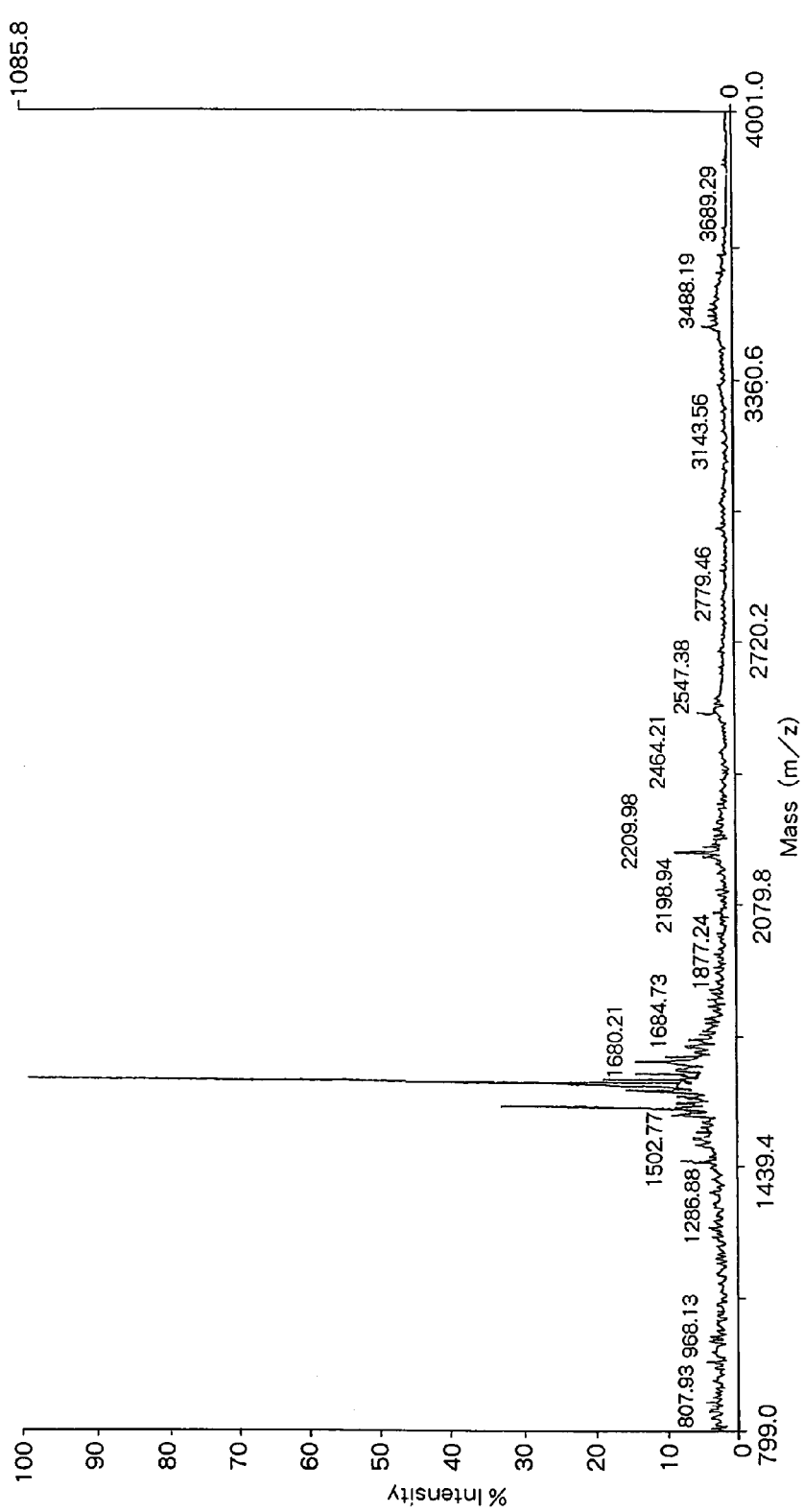
FIG. 6 is a chart showing an example of the mass spectrometry spectrum measured in anionic species detection mode by a MALDI-TOF-MS apparatus for the resulting peptide fragments that are obtained by the treatment process for successive release of C-terminal amino acids from the peptide according to the second aspect of the present invention, in which successive release of C-terminal amino acids of the globin peptide chain was conducted for a sample of horse myoglobin bound on the gel, and then the obtained mixture of reaction products was subjected to the digestion by trypsin.

In Example 2 as well, when there are compared the spectrum in the positive mode detection shown in FIG. 5 and the spectrum in the negative mode detection shown in FIG. 6, there are found, as two main peaks corresponding to the fragments due to digestion by trypsin, which are derived from the globin peptide chain of horse myoglobin, fragments each containing a partial amino acid sequence of 1-31 amino acids or a partial amino acid sequence of 140-153 amino acids, in such a molecular weight range. In the positive mode detection shown in FIG. 5, the peak of high relative intensity is judged to correspond to a N-terminal side peptide fragment having a partial amino acid sequence of 1-31 amino acids and having an arginine residue at the C-terminus and, in the negative mode detection shown in FIG. 6, the peak of high relative intensity is judged to correspond to a C-terminal side peptide fragment having a partial amino acid sequence of 140-153 amino acids and containing no arginine residue. There is further found a peptide fragment corresponding to a partial amino acid sequence of 78-102 amino acids, which is derived from partial amino acid sequence of 32-139 amino acids, by cleavage at the N-acetylation-dropped-off lysine residue therein; in the positive mode detection shown in FIG. 5, the intensity thereof exhibits a relatively high peak. Besides, peptide fragments resulting from trypsin autolysis are also found in such a molecular weight range and, in the positive mode detection shown in FIG. 5, their intensities give relatively high peaks as well.

In the negative mode detection shown in FIG. 6, in addition to the C-terminal side peptide fragment of the partial amino acid sequence of 140-153 amino acids, the intensities for a series of C-terminal side peptide fragments derived from reaction products formed by successive release of C-terminal amino acids are also detected to be relatively high. In Table 2 are shown the measured masses of the peaks, their differences from the mass of peak of C-terminal fragment of original globin peptide chain, as well as the amino acids identified therefrom which are removed in individual reaction product fragments and the forms of individual reaction products.

TABLE 2

| m/Z | Δm | Assignment | Corresponding peptide structure |
|---|---|---|---|
| 1636.55 | — | | NDIAAK(Ac)YK(Ac)ELGFGQ |
| 1578.49 | 58.06 | -Gly | NDIAAK(AC)YK(Ac)ELGFG |
| 1450.52 | 186.03 | -Gln-Gly | NDIAAK(Ac)YK(Ac)ELGF |

In the process for treatment with use of a reaction reagent solution using a dipolar aprotic solvent of the present Example 2, there are identified as well peaks derived from the reaction products in which the two amino acids; i.e. glycine and glutamine are sequentially eliminated from the C-termini thereof by the treatment for the successive release of C-terminal amino acids. That is, it is verified that the to-be-analyzed peptide chain that is separated as a band on the aforementioned gel slice is indeed a globin peptide chain and the successive release of C-terminal amino acids can be conducted in a bound-on-gel state.

It is confirmed that also when there is employed the method for analysis of C-terminal amino acid sequence according to the second aspect of the present invention and the successive release of C-terminal amino acids is conducted in a state that the peptide chain to be analyzed is bound on a gel, substantially comparable analysis accuracy is achieved.

Reference Example 1

In the method for analysis of the C-terminal amino acid sequence of peptide according to the present invention, a peptide chain is subjected to digestion by trypsin in a state that the side chain of lysine residue has been protected by N-acylation and, as a result, whereby the obtained common peptide fragments of N-terminal side amino acid sequence are all the peptide fragmenets having an arginine residue at the C-terminus; this phenomenon is utilized for distinguishment of them from the C-terminal side peptide fragments. It was verified that even if a peptide chain to be analyzed has arginine at the C-terminus, C-terminal side peptide fragments derived from a series of reaction products can be identified by obtaining, as the spectra of the main ion species reflecting the molecular weights of individual peptide fragments in measurement by means of MALDI-TOF-MS apparatus, spectra of proton ($H^+$)-added cationic species in the positive mode detection and spectra of proton ($H^+$)-eliminated anionic species in the negative mode detection and then comparing those two with each other.

In this Reference Example, analysis of the C-terminal amino acid sequence of peptide was conducted for a peptide composed of 14 amino acids wherein the N-terminal amino group of the peptide had been protected by N-acetylation, i.e. an N-acetylated $Glu^1$-Fibrino peptide fragment.

(Operation for Successive Release of C-Terminal Amino Acids)

A vial holding a dried sample of said peptide (Ac-EGVNDNEEGFFSAR) obtained by the treatment for N-acetylation is set in a glass-made reactor of air-tight test tube type with fitting stopper. Into this glass-made reactor is added a predetermined amount of the following liquid reagent.

As the liquid reagent for selective release of C-terminal amino acids, there is used 300 µl of acetic anhydride with 5% by volume of trifluoroacetic acid added thereto. After the vial containing the dried peptide sample is set in the glass-made reactor, the reactor inside is evacuated under cooling condition and then sealed in an air-tight state.

The whole reactor of air-tight state is kept at 40° C. for 16 hours to allow acetic anhydride and trifluoroacetic acid both of vapor phase, supplied from the liquid reagent in the reactor, to act on the dried sample.

After finishing the treatment for selective release of C-terminal amino acids, the unreacted acetic anhydride, trifluoroacetic acid, etc. remaining in the reactor are distilled off under reduced pressure and the resulting mixture of residual N-acetylated $Glu^1$-Fibrino peptide sample and the obtained reaction products is dried.

(Post-Treatment Operation)

Next, in a state that the vial holding the dried sample of a mixture containing the reaction products is set in a glass-made reactor of air-tight test tube type with fitting stopper, a given amount of the following liquid reagent is placed anew in the glass-made reactor.

In this Reference Example 1, as the liquid reagent for the post-treatment for hydrolysis, there is used 300 µl of an aqueous solution in which 10% by volume of pyridine is dissolved; and after the vial containing the dried peptide sample is set in said glass-made reactor, the reactor inside is evacuated under cooling condition and then sealed in an air-tight state.

The whole reactor of air-tight state is kept at 100° C. for 30 minutes to allow pyridine and water molecules both of vapor phase, supplied from the liquid reagent in the reactor, to act on the dried sample. Under such conditions, the protection with O-acetylation to serine residue is deprotected, but hydrolysis for the amide bond of N-terminal protection with N-acetylation does not take place. Therefore, the reaction products obtained by this post-treatment are N-acetylated peptides, which are modified with an acetyl group at the N-termini thereof.

After such post-treatment, the water molecules, pyridine, etc. remaining in the reactor are distilled off under reduced pressure and the resulting mixture of N-acetylated $Glu^1$-Fibrino peptide fragments and the obtained reaction products after post-treatment is dried.

(Identification of Reaction Products Processed by the Post-Treatment)

As for the mixture of the reaction products after post-treatment and the original peptide fragment, which is obtained by the above-mentioned series of chemical treatments, there are obtained by using MALDI-TOF-MS apparatus, two kinds of corresponding spectra as to the main ion species reflecting the molecular weights of individual peptide fragments; i.e. in the positive mode detection, as to proton ($H^+$)-added cationic species and, in the negative mode detection, as to proton ($H^+$)-eliminated anionic species.

Figure 8:
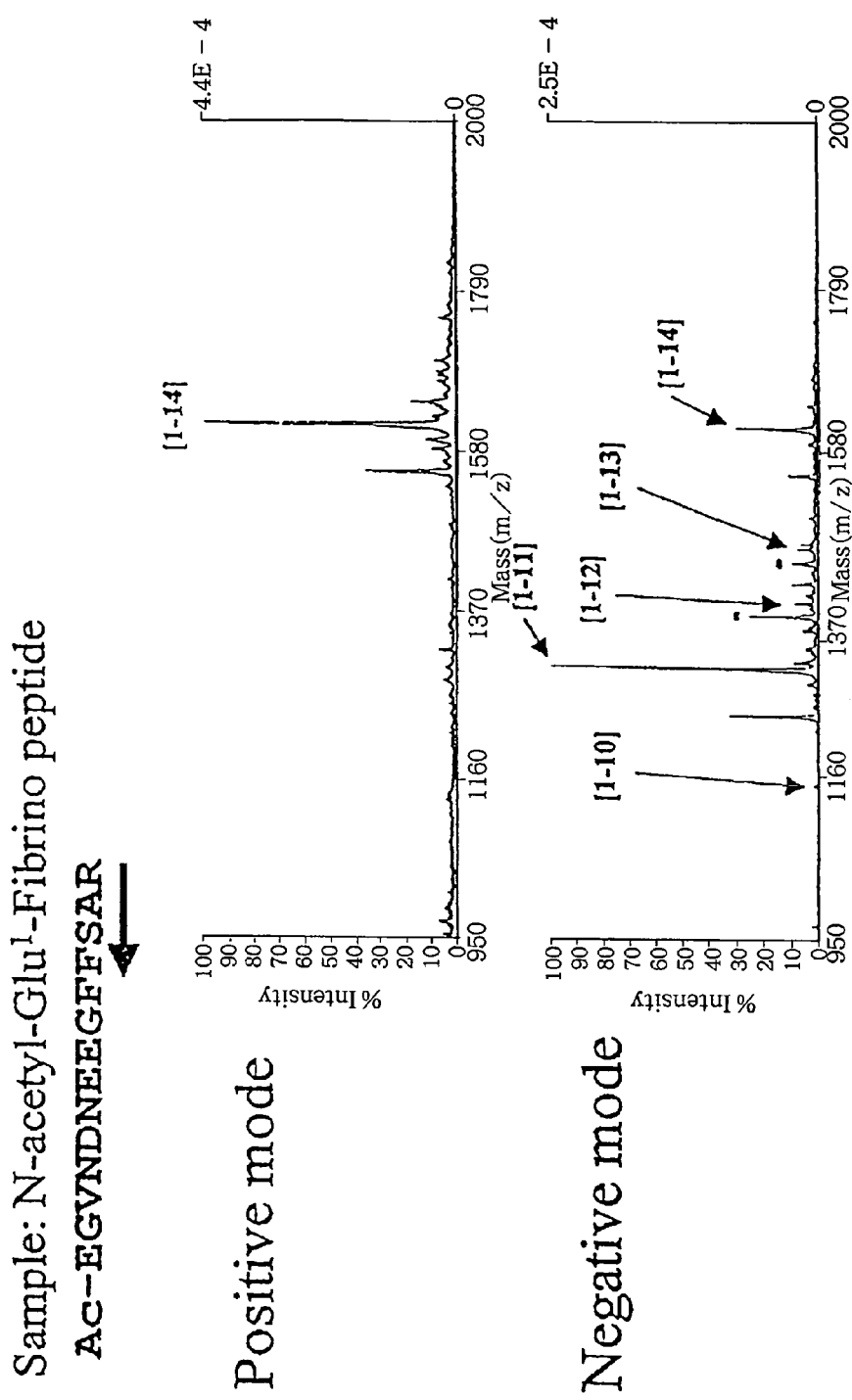
FIG. 8 is a drawing showing a comparison of the MS spectra measured in anionic species detection mode (lower) and in cationic species detection mode (upper) by a MALDI-TOF-MS apparatus for mixture of the resulting reaction products that are obtained by using treatment conditions for successive release of C-terminal amino acids, which conditions are employed in the present invention, in which successive release of C-terminal amino acids of the globin peptide chain was conducted for an isolated dry peptide having an arginine residue at the C-terminus, i.e. an N-acetylated $Glu^1$-Fibrino peptide fragment, as described in Reference Example 1.

The two kinds of spectra shown in FIG. 8 are compared. In the positive mode detection, the intensity for the original peptide fragment having a 1-14 amino acid sequence is relatively high, and it is confirmed that it contains an arginine residue. Furthermore, in the negative mode detection is observed a peak corresponding to the molecular weight in which an arginine residue is eliminated by release; however, in the positive mode detection, no corresponding peak is found clearly. Accordingly, it is confirmed that the original peptide fragment having a 1-14 amino acid sequence has an arginine residue at the C-terminus and the intensity therefor is relatively high in the positive mode detection but, in the negative mode detection, ion species from a series of reaction products, which are accompanying therewith, are found and also there is included a peak corresponding to the molecular weight in which an arginine residue is eliminated by release, which indicates that they undergo the successive release of C-terminal amino acids. In Table 3 are shown the masses of measured peaks, their differences from the mass of peak originated from the original peptide chain, as well as the amino acids identified therefrom which are removed in individual reaction product fragments and the forms of individual reaction products.

TABLE 3

| m/Z | Δm | Assignment | Corresponding peptide structure |
| --- | --- | --- | --- |
| 1610.68 | — | 1–14 | Ac-EGVNDNEEGFFSAR |
| 1454.58 | 156.10 | -Arg | Ac-EGVNDNEEGFFSA |
| 1383.54 | 227.14 | -Ala-Arg | Ac-EGVNDNEEGFFS |
| 1296.51 | 314.17 | -Ser-Ala-Arg | Ac-EGVNDNEEGFF |
| 1149.44 | 461.24 | -Phe-Ser-Ala-Arg | Ac-EGVNDNEEGF |

Thus, even when the amino acid sequence of original peptide chain has arginine at the C-terminus, it is verified that whether it is C-terminal side peptide fragment thereof or other peptide fragments derived from N-terminal side amino acid sequence can be judged at a high accuracy by scrutinizing the presence of the peak indicating the molecular weight decrease corresponding to the elimination of arginine residue, which is associated with the C-terminal side peptide fragment obtained by digestion by trypsin.

INDUSTRIAL APPLICABILITY

In the method for analysis of the C-terminal amino acid sequence of peptide according to the present invention, at the step of successive release of C-terminal amino acids of peptide, employed is such a process in which, in a state that protection with N-acylation is provided beforehand to the N-terminal amino group of the peptide chain and the amino group of the side chain of lysine residue side, and whereby coincidently protection with O-acylation is also provided to the hydroxy groups present in the serine residue (—NH—CH($CH_2OH$)—CO—) and the threonine residue (—NH—CH(CH($CH_3$)OH)—CO—), by acting a reaction reagent that is a combination of an alkanoic acid anhydride and a small amount of a perfluoroalkanoic on a target peptide in a dry atmosphere under a mild temperature condition, release of C-terminal amino acid, which is associated to cleavage of the 5-oxazolone ring following to formation of 5-oxazolone structure, is carried out to prepare a series of reaction products. In such a technique, since the reactivity of the alkanoic acid anhydride used is low, any unnecessary side reaction such as cleavage of amide bond in the middle of peptide is not initiated thereby, and the successive release of C-terminal amino acids of peptide can be performed under a mild heated-up condition therewith. Further, since there is no cleavage of amide bond in the middle of peptide, it is possible to avoid incorporation of peptide fragments secondarily formed by cleavage of amide bond in the middle of peptide or reaction products originating from such secondary peptide fragments into the reaction products obtained. Furthermore, in the post-treatment, hydrolysis is conducted, in the presence of an organic basic compound, for the series of reaction products obtained by means of the reaction of such mild conditions, whereby they are converted to the fragments having each a carboxy group at the C-terminus, in which the protection with o-acylation is deprotected, but the protection with N-acylation on the N-terminal amino group of peptide chain and the amino group of the side chain of lysine residue is kept. Finally, digestion by trypsin is effected to conduct cleavage at the C-terminal side of each arginine residue while avoiding cleavage at the C-terminal side of lysine residue protected with N-acylation, to prepare, from a peptide chain of large amino acid length, C-terminal side peptide fragments of a molecular weight range suitable for detection by means of MALDI-TOF-MS apparatus; thereafter, there can be determined, at a high accuracy, a C-terminal amino acid sequence which is shortened by the successive release of C-terminal amino acids, based on a series of molecular weight decreases in the C-terminal side peptide fragments.

In addition, in the above-mentioned chemical treatment for successive release of C-terminal amino acids, the change in the amino acid length of peptide chain is at most about 10 amino acids; therefore, it is also possible to separate a target peptide by gel electrophoresis and, in a state that the peptide is bound on a gel carrier, advance the afore-mentioned chemical treatments for the peptide. Meanwhile, when digestion by trypsin is effected to give rise to peptide fragmentation, those peptide fragments having remarked short amino acid length can be no longer held on the gel carrier stably and thus it is possible to elute them easily from the gel carrier and recover thereby. Accordingly, since the present method has such advantages as excellent controllability in the successive release of C-terminal amino acids of peptide and mild reaction conditions, for instance, broad width of acceptable variation for the reaction temperature, and enables the analysis of C-terminal amino acid sequence at a high accuracy even for a peptide chain having long amino acid length, the method for analysis of the C-terminal amino acid sequence of peptide according to the present invention can be used as analyzing procedure with wider applicability.

The invention claimed is:

1. A method for analyzing the C-terminal amino acid sequence of a peptide to be examined, which method comprises the following steps:
   a step of preparing a mixture containing a series of reaction products that are obtained from the peptide to be examined by releasing the C-terminal amino acids successively by chemical,
   a step of analyzing the differences in molecular weight between said series of reaction products and the original peptide by means of mass spectrometry to measure the decreases in molecular weight associated with the successive release of the C-terminal amino acids, and
   a step of identifying a series of the amino acids removed successively, based on a series of the measured decreases in molecular weight and arranging them from the C-terminus to obtain the information of the C-terminal amino acid sequence of the peptide,
   wherein said process for releasing the C-terminal amino acids successively, for the sample of the target peptide that has been subjected to separation by gel electrophoresis and is maintained in a state that it is bound on a polyacrylamide gel carrier, comprises the following steps:
   a step of removing the water solvent impregnated into the polyacrylamide gel carrier by dilution with use of a polar aprotic solvent having no solvency for the polyacrylamide gel substance and having affinity for water, to conduct a dehydration treatment for the gel carrier,
   a pretreatment step for the target peptide sample that is still bound on the polyacrylamide gel carrier after carrying out said step for dehydration treatment, in which pretreatment step
   applying N-acylation protection by the acyl group derived from the alkanoic acid constituting said alkanoic acid anhydride, to the N-terminal amino group of the target peptide with use of a solution of the alkanoic acid anhydride dissolved in a dipolar aprotic solvent that is capable of infiltrating into the polyacrylamide gel substance and keeping it in a swollen state is conducted by immersing, at a temperature selected in a range of 30° C. to 80° C., the polyacrylamide gel carrier in the solution of the alkanoic acid anhydride to allow the alkanoic acid anhydride to act on the target peptide sample that is kept in the bound state; and then
   removal of said solution is carried out by dilution with use of a polar aprotic solvent having no solvency for the polyacrylamide gel substance and having affinity for the alkanoic acid anhydride as well as the dipolar aprotic solvent, to conduct termination of the N-acylation reaction and removal of the reaction reagent therefor;
   a step of treatment for the target peptide sample bound on the polyacrylamide gel carrier, after the pretreatment step of N-acylation protection, comprising steps of:
   immersing, at a temperature selected in a range of 30° C. to 80° C., the gel carrier in a mixed solution of an alkanoic acid anhydride added with a small amount of a perfluoroalkanoic acid in relative ratio thereto dissolved in a dipolar aprotic solvent that is capable of infiltrating into the polyacrylamide gel substance and keeping it in a swollen state, to allow the alkanoic acid anhydride and the perfluoroalkanoic acid to act on the target peptide sample being kept in the bound state; thereby, successive release of the C-terminal amino acids results from the reaction process with use of the mixed solution in which the formation of a 5-oxazolone-ring structure represented by the following general formula (III):

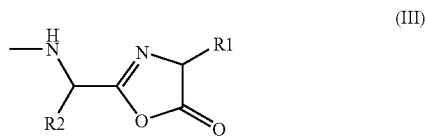

wherein R1 is a side chain of the C-terminal amino acid of the peptide and R2 is a side chain of the amino acid residue positioned just before the C-terminal amino acid, is followed by the cleavage of the 5-oxazolone-ring, and
   removing the mixed solution used in the reaction for successive release of C-terminal amino acids, by dilution with use of a polar aprotic solvent having no solvency for polyacrylamide the gel substance and having affinity for the perfluoroalkanoic acid and the alkanoic acid anhydride as well as the dipolar aprotic solvent, to conduct termination of the releasing reaction and removal of the reaction reagents therefor; and
   an additional step for hydrolysis treatment and then re-dehydration treatment, in which step the hydrolysis treatment for said mixture comprising a series of reaction products obtained by the reaction for successive release of C-terminal amino acids is conducted by immersing the polyacrylamide gel carrier in an aqueous solution dissolving a basic nitrogen-containing aromatic compound or a tertiary amine compound therein to allow a water molecule to act, in the presence of said basic nitrogen-containing organic compound, on said peptides of the reaction products being still bound on the polyacrylamide gel carrier, and then, the re-dehydration treatment for the gel carrier is performed by removing said aqueous solution infiltrated into the polyacrylamide gel carrier by dilution with use of a polar aprotic solvent having no solvency for the gel substance and having affinity for water; and wherein said step of measuring the decreases in molecular weight associated with the successive release of the C-terminal amino acids employs a technique which comprises:

allowing trypsin to act on said mixture, after the re-dried up treatment, containing a series of the reaction products finished by hydrolysis treatment, in a buffer solution, to carry out the treatment for the enzymatic digestion specific to trypsin of said peptide chain which holds N-acylation protection as for the N-terminal amino group of the peptide chain as well as to the amino group on the side chain of the lysine residue that may be contained in the peptide chain, and thereby, conducting selective cleavage of the C-terminal side peptide bond of each arginine residue that is present in the peptide chain to complete peptide fragmentation, applying a desalting treatment to remove the buffer solution component, followed by recovering and drying the peptide fragments after the digestion treatment by trypsin, followed by drying, next to that, conducting, for the dried mixture containing said peptide fragments recovered after the digestion treatment by trypsin, molecular weight measurement for the cationic species of $(M+H)^+$ as well as molecular weight measurement for the anionic species of $(M-H)^-$, both of which are generated from the ionization treatment, by means of MALDI-TOF-MS, with respect to the corresponding ion species, which are measured in said molecular weight measurement for the cationic species of $(M+H)^+$ as well as molecular weight measurement for the anionic species of $(M-H)^-$, judging that the peaks of the peptide fragments each having an arginine residue at the C-terminus, which fragments are produced by said digestion treatment by trypsin, are peaks that give such intensities that the intensity in the molecular weight measurement for the cationic species of $(M+H)^+$ is relatively larger in comparison with the intensity in the molecular weight measurement for the anionic species of $(M-H)^-$, and judging that the peaks of the C-terminal peptide fragment derived from the original peptide and the C-terminal peptide fragments derived from a series of the reaction products that are obtained by successive release of the C-terminal amino acids, which fragments are produced by said digestion treatment by trypsin, are peaks that give such intensities that the intensity in the molecular weight measurement for the anionic species of $(M-H)^-$ is relatively larger in comparison with the intensity in the molecular weight measurement for the cationic species of $(M+H)^+$, and based on a series of the peaks that gives a relatively larger intensity in the molecular weight measurement for the anionic species of $(M-H)^-$, measuring the decreases in molecular weight associated with the successive release of the C-terminal amino acids.

2. A method claimed in claim 1, wherein a symmetric anhydride of an alkanoic acid having 2 to 4 carbon atoms is used as the alkanoic acid anhydride contained in the mixed solution where a small amount of the perfluoroalkanoic acid in relative ratio to the alkanoic acid anhydride is dissolved.

3. A method claimed in claim 2, wherein a symmetric anhydride of a linear chain alkanoic acid having 2 to 4 carbon atoms is used as the symmetric anhydride of said alkanoic acid having 2 to 4 carbon atoms.

4. A method claimed in claim 1, wherein acetic anhydride is used as the alkanoic acid anhydride contained in the mixed solution where a small amount of the perfluoroalkanoic acid in relative ratio to the alkanoic acid anhydride is dissolved.

5. A method claimed in claim 1, wherein a perfluoroalkanoic acid of which a pKa is in the range of 0.3 to 2.5 is used as the perfluoroalkanoic acid contained in the mixed solution where a small amount of the perfluoroalkanoic acid in relative ratio to the alkanoic acid anhydride is dissolved.

6. A method claimed in claim 1, wherein a perfluoroalkanoic acid having 2 to 4 carbon atoms is used as the perfluoroalkanoic acid contained in the mixed solution where a small amount of the perfluoroalkanoic acid in relative ratio to the alkanoic acid anhydride is dissolved.

7. A method claimed in claim 6, wherein a linear chain perfluoroalkanoic acid having 2 to 4 carbon atoms is used as the perfluoroalkanoic acid having 2 to 4 carbon atoms in the mixed solution where a small amount of the perfluoroalkanoic acid in relative ratio to the alkanoic acid anhydride is dissolved.

8. A method claimed in claim 1, wherein, in the mixed solution where a small amount of the perfluoroalkanoic acid in relative ratio to the alkanoic acid anhydride is dissolved, the content ratio of the alkanoic acid anhydride and the perfluoroalkanoic acid is selected in the range of 1 to 20 volumes of the perfluoroalkanoic acid per 100 volumes of the alkanoic acid anhydride.

* * * * *